(12) United States Patent
Ogata et al.

(10) Patent No.: US 7,723,007 B2
(45) Date of Patent: May 25, 2010

(54) POLYMER COMPOUND, PHOTORESIST COMPOSITION INCLUDING THE POLYMER COMPOUND, AND RESIST PATTERN FORMATION METHOD

(75) Inventors: Toshiyuki Ogata, Kawasaki (JP); Syogo Matsumaru, Kawasaki (JP); Yohei Kinoshita, Kawasaki (JP); Hideo Hada, Kawasaki (JP); Daiju Shiono, Kawasaki (JP); Hiroaki Shimizu, Kawasaki (JP); Naotaka Kubota, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 472 days.

(21) Appl. No.: 10/589,681

(22) PCT Filed: Jan. 28, 2005

(86) PCT No.: PCT/JP2005/001228
§ 371 (c)(1),
(2), (4) Date: Aug. 16, 2006

(87) PCT Pub. No.: WO2005/080473
PCT Pub. Date: Sep. 1, 2005

(65) Prior Publication Data
US 2008/0166655 A1 Jul. 10, 2008

(30) Foreign Application Priority Data

| Feb. 20, 2004 | (JP) | 2004-045522 |
| Apr. 28, 2004 | (JP) | 2004-134585 |
| Jun. 17, 2004 | (JP) | 2004-179475 |
| Aug. 31, 2004 | (JP) | 2004-252474 |
| Oct. 29, 2004 | (JP) | 2004-316960 |

(51) Int. Cl.
G03F 7/004 (2006.01)
C07C 61/26 (2006.01)
C08F 32/08 (2006.01)

(52) U.S. Cl. ............ 430/270.1; 430/907; 430/910; 526/281; 526/284; 560/220

(58) Field of Classification Search .......... 430/270.1, 430/281.1, 910, 907; 560/220
See application file for complete search history.

(56) References Cited

U.S. PATENT DOCUMENTS

| 6,027,856 | A | 2/2000 | Nozaki et al. | |
| 6,042,991 | A * | 3/2000 | Aoai et al. | 430/270.1 |
| 6,329,125 | B2 | 12/2001 | Takechi et al. | |
| 6,579,659 | B2 * | 6/2003 | Uetani et al. | 430/270.1 |
| 6,830,871 | B2 * | 12/2004 | Kanna et al. | 430/285.1 |
| 7,189,493 | B2 * | 3/2007 | Hatakeyama et al. | 430/270.1 |
| 7,402,712 | B2 * | 7/2008 | Hatakeyama et al. | 568/665 |
| 2002/0099147 | A1 * | 7/2002 | Yoshida et al. | 525/329.7 |
| 2002/0177068 | A1 * | 11/2002 | Park et al. | 430/270.1 |
| 2003/0008232 | A1 | 1/2003 | Kinsho | |
| 2003/0219677 | A1 | 11/2003 | Namba et al. | |
| 2003/0224289 | A1 * | 12/2003 | Choi et al. | 430/270.1 |
| 2004/0053161 | A1 * | 3/2004 | Kanna et al. | 430/270.1 |
| 2005/0004391 | A1 * | 1/2005 | Hatakeyama et al. | 560/220 |
| 2005/0079446 | A1 * | 4/2005 | Hatakeyama et al. | 430/281.1 |
| 2006/0160247 | A1 * | 7/2006 | Koyama et al. | 438/1 |
| 2007/0148594 | A1 * | 6/2007 | Funatsu et al. | 430/270.1 |

FOREIGN PATENT DOCUMENTS

| DE | 19912047 | | 11/1999 |
| EP | 1 262 830 | A | 12/2002 |
| GB | 2 320 717 | A | 7/1998 |
| JP | H11-305439 | | 11/1999 |
| JP | 2001-318465 | | 11/2001 |
| JP | 2003-21839 | | 1/2003 |
| JP | 2003-221420 | | 8/2003 |
| JP | 2005-17729 | | 1/2005 |
| WO | WO 94/17057 | A | 8/1994 |

OTHER PUBLICATIONS

Ogata, Toshiyuki., Matsumaru,. S., Shimizu, H. Kubota, N., Hada, H. and Shirai, M. Effects of Protecting Group on Resist Characteristics of Acryl Polymers for 193 mn Lithography. Jun. 2004, Journal of Photopolymer Science and Technology, vol. 17, No. 4. pp. 483-488.*
Hagiwara et al. "Characterization of Fluoropolymer Resist for 157-nm Lithography." *Journal of Photopolymer Science and Technology*. 16(4):557-564 (2003).
Houlihan et al. "New Flourinated Resins for 167nm Lithography Application." *Journal of Photopolymer Science and Technology*. 16(4):581-590 (2003).
Kawaguchi et al. "Dry-Etching Resistance for Fluoropolymers for 157-nm Single-Layer Resists." *Proceedings of SPIE*. 5039:43-52 (2003).
Written Opinion and Search Report issued on Apr. 14, 2008, on the counterpart Singapore Patent Application No. 200605551-1.
Supplementary European search report issued in corresponding European Patent Application No. EP 05709454.2, dated Jan. 27, 2010.

* cited by examiner

*Primary Examiner*—John S Chu
(74) *Attorney, Agent, or Firm*—Knobbe, Martens, Olson & Bear, LLP

(57) ABSTRACT

The present invention provides a polymer compound which can constitute a photoresist composition which is capable of having an excellent resolution, forming a fine pattern with a good rectangularity, obtaining favorable resist characteristics even when acid strength of a acid generated from an acid generator is weak, and having favorable sensitivity; a photoresist composition including the polymer compound; and a resist pattern formation method using the photoresist composition. The photoresist composition and the resist pattern formation method use the polymer compound including an alkali soluble group (i), wherein the alkali soluble group (i) is at least one substituent group selected from an alcoholic hydroxyl group, a carboxyl group, or a phenolic hydroxyl group, and the substituent group is protected by an acid dissociable, dissolution inhibiting group (ii) represented by a general formula (1):

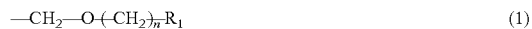

$$-CH_2-O-(CH_2)_n-R_1 \quad (1)$$

(wherein $R_1$ represents a cycloaliphatic group which contains no more than 20 carbon atoms and may contain an oxygen atom, a nitrogen atom, a sulfur atom, or a halogen atom, and n represents 0 or an integer of 1 to 5).

13 Claims, 1 Drawing Sheet

US 7,723,007 B2

POLYMER COMPOUND, PHOTORESIST COMPOSITION INCLUDING THE POLYMER COMPOUND, AND RESIST PATTERN FORMATION METHOD

CROSS-REFERENCE TO RELATED APPLICATIONS

This application is the U.S. National Phase filing under 35 U.S.C. §371 of PCT/JP2005/001228, filed Jan. 28, 2005, which designated the United States and was published in a language other than English, which claims priority under 35 U.S.C. §119(a)-(d) to Japanese Patent Application Nos. 2004-045522, filed Feb. 20, 2004; 2004-134585, filed Apr. 28, 2004; 2004-179475, filed Jun. 17, 2004; 2004-252474, filed Aug. 31, 2004; and 2004-316960, filed Oct. 29, 2004. The content of these applications is incorporated herein by reference in their entireties.

TECHNICAL FIELD

The present invention relates to a polymer compound; a low molecular weight compound which is preferable for preparing the polymer compound; a photoresist composition including the polymer compound; and a resist pattern formation method.

Priority is claimed on Japanese Patent Application No. 2004-045522, filed Feb. 20, 2004; Japanese Patent Application No. 2004-134585, filed Apr. 28, 2004; Japanese Patent Application No. 2004-179475, filed Jun. 17, 2004; Japanese Patent Application No. 2004-252474, filed Aug. 31, 2004; and Japanese Patent Application No. 2004-316960, filed Oct. 29, 2004, the contents of which are incorporated herein by reference.

BACKGROUND ART

It is no exaggeration that miniaturization of a semiconductor integrated circuit pattern has been accomplished due to the progress of photolithography and peripheral techniques thereof. This photolithography includes two generally known main techniques. One is a technique on an exposure wavelength or a numerical aperture of a reduction projection exposure apparatus known as a stepper or a scanner. The other is a technique on resist characteristics such as printing resolution of a photoresist composition in which a mask pattern is printed by the aforementioned reduction projection exposure apparatus. These have improved processing accuracy of a semiconductor integrated circuit pattern by means of photolithography.

The wavelength of light sources used in the reduction projection exposure apparatus has been increasingly shortened in response to a demand for high resolution circuit patterns. In general, the g-line (436 nm) or i-line (365 nm) of a mercury lamp is used in the case of a resist resolution of about 0.5 µm or 0.30 to about 0.5 µm, respectively. The main spectra of the g-line and i-line are 436 nm and 365 nm, respectively. Also, a KrF excimer laser (248 nm) and an ArF excimer laser (193 nm) are used in the case of a resist resolution of 0.15 to about 0.30 µm, or about 0.15 µm or less, respectively. Furthermore, use of an $F_2$ excimer laser (157 nm), an $Ar_2$ excimer laser (126 nm), and EUV (extreme ultraviolet light, wavelength: 13 nm) is being investigated in order to further miniaturize a semiconductor integrated circuit pattern.

As far as a photoresist composition is concerned, the life of a photoresist for KrF in lithography using a KrF excimer laser is currently prolonged by combining this photoresist with an organic or inorganic anti-reflective film or by devising an exposure system, and the photoresist composition with an eye to about 110 nm, which is below $\lambda/2$, is being developed. Also, provision of a photoresist composition for ArF has been desired, which is preferable for the mass production of a prospective fine pattern with a node of about 90 nm or less in lithography using an ArF excimer laser. Furthermore, lithography using the aforementioned $F_2$ excimer laser has drawn attention as a technique for processing a prospective fine pattern with a node of 65 nm or less, and a photoresist composition is being developed which is applicable to fine processing by lithography using an $F_2$ excimer laser.

Since it is difficult for a conventional positive photoresist including an alkali soluble novolak resin and a quinone diazide group-containing compound as main components to achieve such a fine pattern, a photoresist applicable to a far-UV ray with a further shortened wavelength (200 to 300 nm); an excimer laser such as KrF, ArF, or $F_2$; an electron beam; and X ray has been desired to be developed. As such a photoresist, a chemically amplified resist has drawn attention and is being actively developed, in which a catalytic reaction and a chain reaction due to an acid generated on exposure to radiation can be realized, the quantum yield is 1 or higher, and high resolution and sensitivity can be achieved.

A resin containing an acid dissociable, dissolution inhibiting group is mainly used in a positive chemically amplified resist.

Examples of an acid dissociable, dissolution inhibiting group used in the chemically amplified resist include an acetal group, a tertiary alkyl group such as a tert-butyl group, tert-butoxycarbonyl group, and tert-butoxycarbonylmethyl group as an acid dissociable, dissolution inhibiting group for a fluorinated alcohol as disclosed in the following non-patent references 1 to 3.

Also, as described in the following patent reference 1, a structural unit derived from a tertiary ester compound of (meth)acrylic acid, for example 2-alkyl-2-adamantyl (meth)acrylate, is generally used as a structural unit containing an acid dissociable, dissolution inhibiting group in a resin component of a conventional ArF resist composition. In the present specification, "acrylic acid" and "methacrylic acid" are collectively referred to as "(meth)acrylic acid", "acrylic acid derivative" and "methacrylic acid derivative" are collectively referred to as "(meth)acrylic acid derivative", and "acrylate" and "methacrylate" are collectively referred to as "(meth)acrylate".

However, an acid dissociable, dissolution inhibiting group used in these chemically amplified resists disclosed in non-patent references 1 to 3 has a problem in terms of the improvement of resolution and the formation of a fine pattern with a good rectangularity because an alkali dissolution inhibiting effect in a unexposed part is insufficient (thickness loss occurs in a resist pattern). Provided that an introduction rate of an acid dissociable, dissolution inhibiting group is increased to improve an alkali dissolution inhibiting effect in a unexposed part, there is another problem in that the risk of defect is increased.

Also, as described in the patent reference 1, a compound forming a cyclic or linear tertiary alkyl ester with a carboxyl group of (meth)acrylic acid is well-known as a compound forming an acid dissociable, dissolution inhibiting group. However, there is a limitation to the number of types of an available acid generator. In other words, there is a problem of not working as a chemically amplified positive resist because an acid dissociable, dissolution inhibiting group is not dissociated unless an acid generator is used, in which acid strength of a generated acid is strong, for example an onium salt containing a fluorinated alkylsulfonic acid ion at an anion part. Also, there is another problem in that sensitivity is not sufficient when an acid generator is used, in which acid strength of a generated acid is weak. The improvement of these problems has highly been desired.

[Non-Patent Reference 1]

T. Hagiwara, S. Irie, T. Itani, Y. Kawaguchi, O. Yokokoji, S. Kodama, J. Photopolym. Sci. Technol. Vol. 16, Page 557, 2003

[Non-Patent Reference 2]

F. Houlihan, A. Romano, D. Rentkiewicz, R. Sakamuri, R. R. Dammel, W. Conley, G. Rich, D. Miller, L. Rhodes, J. McDaniels, C. Chang, J. Photopolym. Sci. Technol. Vol. 16, Page 581, 2003

[Non-Patent Reference 3]

Y. Kawaguchi, J. Irie, S. Kodama, S. Okada, Y. Takebe, I. Kaneko, O. Yokokoji, S. Ishikawa, S. Irie, T. Hagiwara, T. Itani, Proc. SPIE, Vol. 5039, Page 43, 2003

[Patent Reference 1]

Japanese Unexamined Patent Application, First Publication No. Hei10-161313

DISCLOSURE OF INVENTION

The present invention has been accomplished in consideration of the aforementioned problems, and an object of the present invention is to provide a polymer compound which can constitute a photoresist composition capable of having an excellent resolution, forming a fine pattern with a favorable rectangularity, obtaining favorable resist characteristics even when acid strength of an acid generated from an acid generator is weak, and having favorable sensitivity. Also, other objects of the present invention are to provide a compound preferable for preparing the polymer compound, a photoresist composition including the polymer compound, and a resist pattern formation method using the photoresist composition.

To achieve the aforementioned objects, the present inventors have conducted intensive research in which various acid dissociable, dissolution inhibiting groups were introduced into an alkali soluble group of a polymer compound for a photoresist composition as a protecting group, and the resist characteristics of these polymer compounds were investigated. Then, for the first time, it was found in the case of using an acid dissociable, dissolution inhibiting group containing a specific cycloaliphatic group that a fine pattern with a favorable resist pattern shape and improved resolution can be formed. The present invention has been completed on the basis of the above knowledge. In addition, it was also found in the case of using an acid dissociable, dissolution inhibiting group containing a specific cycloaliphatic group that more choices of an acid generator and a highly sensitive resist composition can be obtained in comparison with the case of forming an acid dissociable, dissolution inhibiting group by using a conventional compound which forms a cyclic or linear tertiary alkylester with a carboxyl group of (meth)acrylic acid.

A polymer compound of present invention includes an alkali soluble group (i), wherein at least one hydrogen atom of the alkali soluble group (i) is substituted by an acid dissociable, dissolution inhibiting group (ii) represented by a general formula (1):

(1)

(wherein $R_1$ represents a cycloaliphatic group which contains no more than 20 carbon atoms and may contain an oxygen atom, a nitrogen atom, a sulfur atom, or a halogen atom (hereinafter, these atoms are collectively referred to as a "heteroatom"), and n represents 0 or an integer of 1 to 5), and the polymer compound exhibits changed alkali solubility under the action of an acid.

It is preferable that the alkali soluble group (i) be at least one selected from an alcoholic hydroxyl group, a phenolic hydroxyl group, or a carboxyl group. When the alkali soluble group (i) is an alcoholic hydroxyl group, it is more preferable that a carbon atom adjacent to the carbon atom bonded to the alcoholic hydroxyl group be bonded to at least one fluorine atom.

It is preferable that $R_1$ in the general formula (1) represent a cycloaliphatic group which contains no more than 20 carbon atoms, may contain a heteroatom, and contains an adamantane backbone. Moreover, it is preferable that $R_1$ represent a cycloaliphatic group containing at least one hydrophilic group, and that the hydrophilic group be at least one selected from the group consisting of a carbonyl group, an ester group, an alcoholic hydroxyl group, ether, an imino group, and an amino group.

A novel compound of the present invention is represented by a general formula (2):

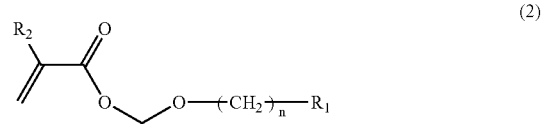

(2)

(wherein $R_1$ and n represent the same as the aforementioned; and $R_2$ represents a hydrogen atom, a fluorine atom, a lower alkyl group containing 1 to 20 carbon atoms, or a fluorinated lower alkyl group containing 1 to 20 carbon atoms), and a polymer compound containing a structural unit (a1) derived from the compound represented by the general formula (2) is included in a polymer compound of the present invention.

A photoresist composition of the present invention includes a base material resin component (A) (hereinafter, may be referred to as a "component (A)") which exhibits changed alkali solubility under the action of an acid; and an acid generator component (B) (hereinafter, may be referred to as a "component (B)") which generates the acid on exposure to radiation, wherein the base material resin component (A) is a polymer compound of the present invention.

A resist pattern formation method of the present invention includes forming a photoresist film on a substrate using a photoresist composition of the present invention; exposing the photoresist film; and developing the exposed photoresist film to form a resist pattern.

According to the present invention, it is possible to provide a fine pattern with high resolution and a favorable resist pattern shape (rectangularity). Also, an acid dissociable, dissolution inhibiting group can be dissociated by even an acid generator generating an acid whose acid strength is weak, and it is possible to obtain favorable sensitivity.

BEST MODE FOR CARRYING OUT THE INVENTION

Figure 1:
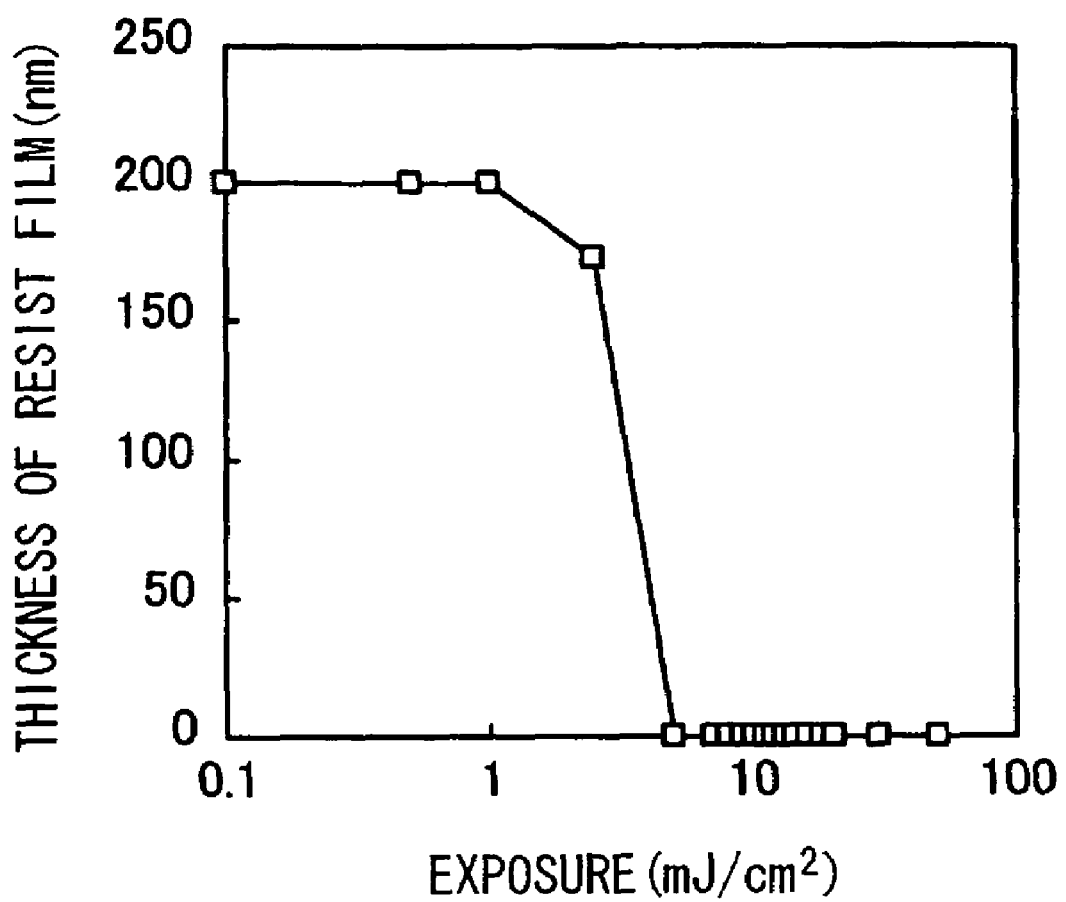
FIG. 1 is a figure showing the sensitivity profile obtained by using ArF exposure in Example 4.

A detailed description of the present invention is as follows.

In the present claims and specification, a "structural unit" means a monomer unit constituting a polymer compound.

In the present claims and specification, an alkyl group, an alkoxy group, or an alkylene group may be linear or branched unless otherwise noted.

In a polymer compound of present invention, at least one hydrogen atom of an alkali soluble group (i) in this molecule is substituted by an acid dissociable, dissolution inhibiting group (ii) represented by a general formula (3):

(3)

(wherein $R_1$ represents a cycloaliphatic group which contains no more than 20 carbon atoms and may contain a heteroatom, and n represents 0 or an integer of 1 to 5).

When a polymer compound of the present invention is used in the system of a chemically amplified positive resist, a dissolution inhibiting effect in an alkali developing solution is shown before exposure, whereas alkali solubility due to deprotection is shown after exposure and a PEB (post exposure baking) process because the polymer compound contains an acid dissociable, dissolution inhibiting group (ii) containing a cycloaliphatic group represented by the aforementioned general formula (1) or (3).

Since the alkali solubility is greatly changed before and after exposure in the chemically amplified positive resist, it is possible to provide a fine pattern excellent in resolution. Also, a polymer compound of the present invention improves etching resistance. In particular, when a hydrophilic group is further introduced into an acid dissociable, dissolution inhibiting group (ii), the adhesion of a resist pattern to a substrate is improved, and the affinity of a resist pattern to an alkali developing solution is improved, thereby reducing the developing defects. Also, mask linearity becomes favorable.

[Acid Dissociable, Dissolution Inhibiting Group (ii)]

An alkali soluble group (i) is described below in detail. An alkali soluble group (i) contains a hydrogen atom which is substituted by an acid dissociable, dissolution inhibiting group (ii). In other words, when an alkali soluble group (i) is an alcoholic hydroxyl group, a carboxyl group, or a phenolic hydroxyl group, an acid dissociable, dissolution inhibiting group (ii) is bonded to the oxygen atom of the alkali soluble group (i) in which one hydrogen atom has been removed.

The acid dissociable, dissolution inhibiting group (ii) is represented by the general formula (1). In the general formula (1), $R_1$ represents a cycloaliphatic group which may contain a heteroatom and contains no more than 20 carbon atoms, preferably 2 to 20 carbon atoms, more preferably 3 to 20 carbon atoms, most preferably 5 to 12 carbon atoms. The cycloaliphatic group may contain a substituent group. A value of n is preferably 0 or 1.

The word "aliphatic" in the present claims and specification is defined as a relative conception to the word "aromatic", which means a non-aromatic group or compound. A "cycloaliphatic group" means a non-aromatic monocyclic group or polycyclic group (alicyclic group). A "cycloaliphatic group" is not limited to a group composed of carbon and hydrogen, although a hydrocarbon group is preferable. Also, a "hydrocarbon" can be saturated or unsaturated although it is usually preferable that a "hydrocarbon" be saturated.

Examples of the cycloaliphatic group include a monovalent group derived from cyclohexane, cyclopentane, adamantane, norbornane, norbornene, methylnorbornane, ethylnorbornane, methylnorbornene, ethylnorbornene, isobornane, tricyclodecane, or tetracyclododecane. The cycloaliphatic group can be appropriately selected to be used from among many cycloaliphatic groups having been proposed in an ArF resist. Among them, a cyclohexyl group, a cyclopentyl group, an adamantyl group, a norbornyl group, a norbornenyl group, a methylnorbornyl group, an ethylnorbornyl group, a methylnorbornenyl group, an ethylnorbornenyl group, or a tetracyclododecanyl group is industrially preferable, and an adamantyl group is most preferable.

It is more preferable that $R_1$ in the general formula (1), which represents the acid dissociable, dissolution inhibiting group (ii), represent a cycloaliphatic group containing at least one hydrophilic group. It is preferable that the hydrophilic group be a carbonyl group (preferably a ketonic carbonyl group), an ester group (—COOR), an alcoholic hydroxyl group, ether (—OR), an imino group, and an amino group, and a carbonyl group is most preferable because it is easily available.

Examples of the acid dissociable, dissolution inhibiting group (ii) include the groups represented by the following chemical formulae (4) to (15).

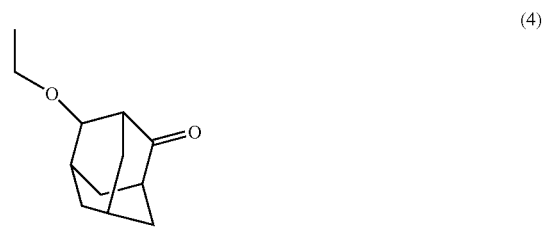
(4)

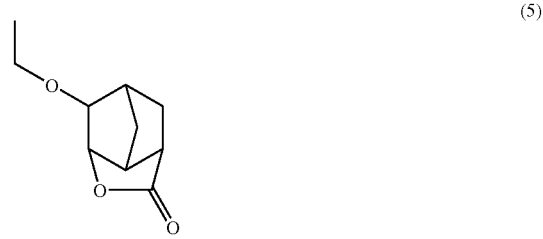
(5)

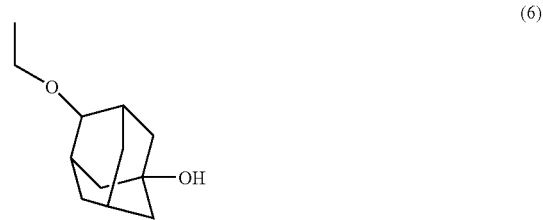
(6)

(7)

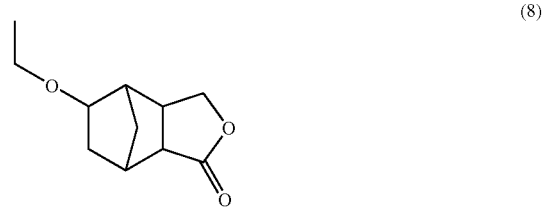
(8)

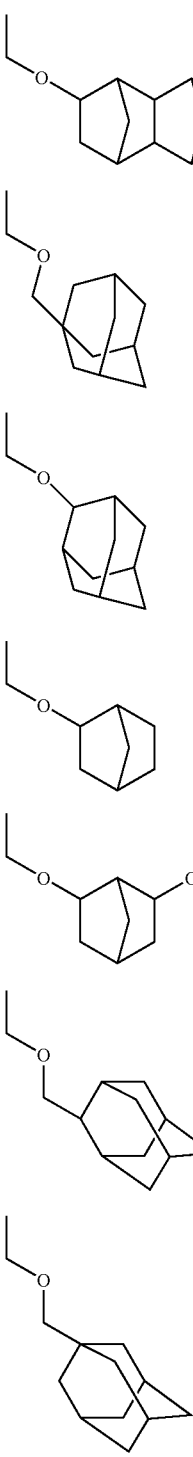

(9)
(10)
(11)
(12)
(13)
(14)
(15)

[Alkali Soluble Group (i)]

An alkali soluble group (i) in a polymer compound of the present invention is known because examples are cited in the aforementioned non-patent references, and a KrF resist, an ArF resist, and an $F_2$ resist have been proposed. These generally known examples can be used as an alkali soluble group (i). Examples of the alkali soluble group (i) include an alcoholic hydroxyl group, a phenolic hydroxyl group, and a carboxyl group, and there is no limitation to these groups.

In the present invention, it is preferable that the alkali soluble group (i) be at least one selected from an alcoholic hydroxyl group, a phenolic hydroxyl group, or a carboxyl group. Among them, an alcoholic hydroxyl group is preferable because it has high transparency and appropriate alkali solubility. Also, among alcoholic groups, it is more preferable that a carbon atom adjacent to the carbon atom bonded to the alcoholic hydroxyl group be bonded to at least one fluorine atom.

The alcoholic hydroxyl group can be a simple hydroxyl group, an alcoholic hydroxyl group-containing alkyloxy group, an alcoholic hydroxyl group-containing alkyloxyalkyl group, or an alcoholic hydroxyl group-containing alkyl group. Examples of an alkyloxy group, an alkyloxyalkyl group, and an alkyl group include a lower alkyloxy group, a lower alkyloxy-lower alkyl group, and a lower alkyl group, respectively. Herein, the word "lower" represents 1 to 4 carbon atoms.

Specific examples of the lower alkyloxy group include a methyloxy group, an ethyloxy group, a propyloxy group, and a butyloxy group. Specific examples of the lower alkyloxy-lower alkyl group include a methyloxymethyl group, an ethyloxymethyl group, a propyloxymethyl group, and a butyloxymethyl group. Specific examples of the lower alkyl group include a methyl group, an ethyl group, a propyl group, and a butyl group.

Also, at least one or all of the hydrogen atoms of an alkyloxy, alkyloxyalkyl, or alkyl group in the aforementioned alcoholic hydroxyl group-containing alkyloxy, alcoholic hydroxyl group-containing alkyloxyalkyl, or alcoholic hydroxyl group-containing alkyl group may be substituted by a fluorine atom. Preferable examples include an alcoholic hydroxyl group-containing alkyloxy group in which at least one of the hydrogen atoms of an alkyloxy part is substituted by a fluorine atom, an alcoholic hydroxyl group-containing alkyloxyalkyl group in which at least one of the hydrogen atoms of an alkyloxy part is substituted by a fluorine atom, and an alcoholic hydroxyl group-containing alkyl group in which at least one of the hydrogen atoms of an alkyl group is substituted by a fluorine atom. In other words, preferable examples include an alcoholic hydroxyl group-containing fluoroalkyloxy group, an alcoholic hydroxyl group-containing fluoroalkyloxyalkyl group, or an alcoholic hydroxyl group-containing fluoroalkyl group.

Examples of the alcoholic hydroxyl group-containing fluoroalkyloxy group include a 2-bis(trifluoromethyl)-2-hydroxy-ethyloxy group $((HO)C(CF_3)_2CH_2O-)$ and a 3-bis(trifluoromethyl)-3-hydroxypropyloxy group $((HO)C(CF_3)_2CH_2CH_2O-)$. Examples of the alcoholic hydroxyl group-containing fluoroalkyloxyalkyl group include a $(HO)C(CF_3)_2CH_2O-CH_2-$ group and a $(HO)C(CF_3)_2CH_2CH_2O-CH_2-$ group. Examples of the alcoholic hydroxyl group-containing fluoroalkyl group include a 2-bis(trifluoromethyl)-2-hydroxy-ethyl group $((HO)C(CF_3)_2CH_2-)$ and a 3-bis(trifluoromethyl)-3-hydroxypropyl group $((HO)C(CF_3)_2CH_2CH_2-)$.

Examples of the phenolic hydroxyl group include phenolic hydroxyl groups of a novolak resin and poly-(α-methyl)hydroxystyrene. Among them, a phenolic hydroxyl group of poly-(α-methyl)hydroxystyrene is preferable because it is inexpensive and easily available.

Examples of the carboxyl group include a carboxyl group of a structural unit derived from an ethylenic unsaturated carboxylic acid. Examples of this ethylenic unsaturated carboxylic acid include an unsaturated carboxylic acid such as acrylic acid, methacrylic acid, maleic acid, or fumaric acid. Among them, acrylic acid and methacrylic acid are preferable because they are inexpensive and easily available.

[Compound of the Present Invention and Structural Unit (a1)]

A novel compound of the present invention (may be referred to as a "low molecular weight compound" in comparison with a polymer compound of the present invention) is represented by a following general formula (16):

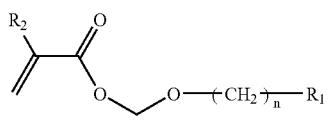

(16)

(wherein $R_2$ represents a hydrogen atom, a fluorine atom, a lower alkyl group containing 1 to 20 carbon atoms, or a fluorinated lower alkyl group containing 1 to 20 carbon atoms; $R_1$ represents a cycloaliphatic group which contains 3 to 20 carbon atoms and may contain a heteroatom; and n represents 0 or an integer of 1 to 5). Also, a polymer compound containing a structural unit (a1) derived from the compound as a monomer unit is included in a polymer compound of the present invention.

The structural unit (a1) corresponds to a structural unit derived from a novel compound of the present invention in which the alkali soluble group (i) is a carboxyl group derived from acrylic acid which may contain a substituent group ($R_2$), and a hydrogen atom of the carboxyl group is substituted by an acid dissociable, dissolution inhibiting group (ii).

In the general formula (16), $R_2$ represents a hydrogen atom, a fluorine atom, a lower alkyl group containing 1 to 20 carbon atoms, or a fluorinated lower alkyl group containing 1 to 20 carbon atoms; preferably a lower alkyl group containing 1 to 4 carbon atoms or a fluorinated lower alkyl group containing 1 to 4 carbon atoms, and examples thereof include a methyl group, an ethyl group, a propyl group, a butyl group, and trifluoromethyl group. Among them, a hydrogen atom and a methyl group are most preferable because they are inexpensive and easily available. A value of n is 0 or an integer of 1 to 5, preferably 0 or 1.

Preferable examples of a compound represented by the general formula (16) include a compound represented by a following general formula (17):

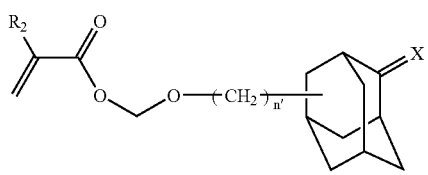

(17)

(wherein $R_2$ represents the same as the aforementioned, X represents two hydrogen atoms or an oxygen atom, and n' represents 0 or 1).

In other words, when X represents two hydrogen atoms, a methylene chain (—$CH_2$—) is formed.

Among compounds represented by the general formula (17), more preferable examples include compounds represented by the following general formulae (18) to (20).

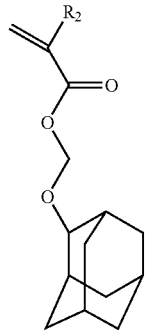

(18)

(wherein $R_2$ represents the same as the aforementioned.)

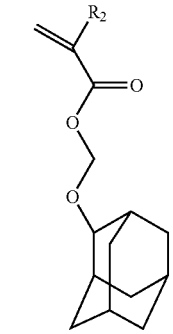

(19)

(wherein $R_2$ represents the same as the aforementioned.)

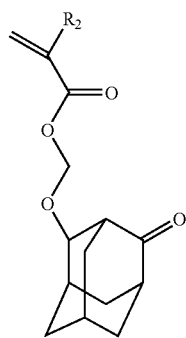

(20)

(wherein $R_2$ represents the same as the aforementioned.)

[Polymer Compound]

The polystyrene equivalent weight average molecular weight (Mw) determined using gel permeation chromatography (GPC) of a polymer compound of the present invention is preferably 5,000 to 80,000, more preferably 8,000 to 50,000 for use in a photoresist composition, although there is no limitation to these ranges. Also, the degree of dispersion (Mw/Mn) is about 1.0 to 5.0, preferably 1.0 to 2.5. Mn is a number average molecular weight.

A precursor of a polymer compound of the present invention before introducing an acid dissociable, dissolution inhibiting group (ii) can be composed of one, or two or more structural units containing an alkali soluble group (i). Hereinafter, as a matter of convenience of explanation, a "precursor" or a "polymer compound" may be referred to as a polymer compound before or after introducing an acid dissociable, dissolution inhibiting group (ii), respectively, so as to distinguish both.

One, or two or more structural units selected from monomer units including the alcoholic hydroxyl group, the phenolic hydroxyl group, and the carboxyl group are used as a structural unit including the alkali soluble group (i). In addition to those, a structural unit including the alkali soluble group (i) can further include a structural unit used in a conventional polymer compound for a photoresist composition.

Examples of a structural unit including the alkali soluble group (i) include structural units containing the alcoholic hydroxyl groups in which a carbon atom adjacent to the carbon atom bonded to the alcoholic hydroxyl group is bonded to at least one fluorine atom as represented by the following chemical formulae (21) to (29); structural units containing a phenolic hydroxyl group as represented by the following chemical formulae (30) to (31); and structural units containing a carboxyl group as represented by the following chemical formulae (32) to (35) and (45) in which $R^7$ represents a hydrogen atom.

Herein, it is preferable that the structural unit represented by the chemical formula (22) be used in combination with a structural unit derived from tetrafluorinated ethylene as represented by the chemical formula (23).

(21)
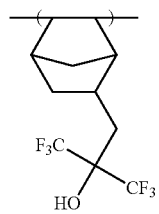

(22)
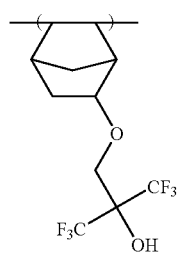

(23)
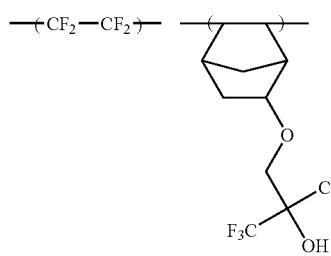

-continued

(24)
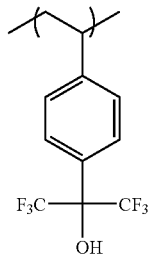

(25)
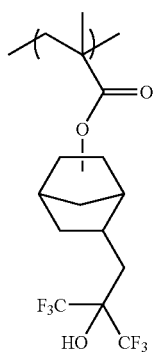

(26)
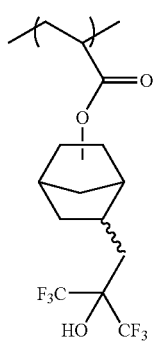

(27)
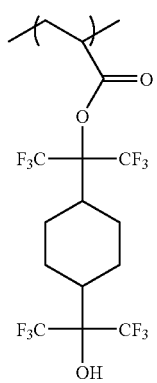

(28)
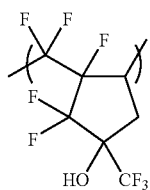

-continued

(29)
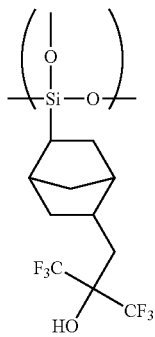

(30)
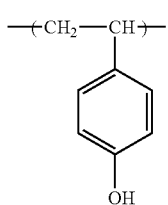

(31)
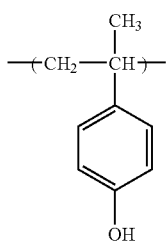

(32)
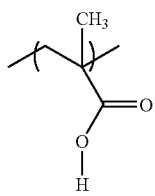

(33)
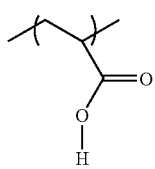

(34)
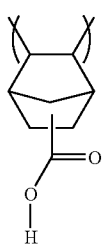

-continued

(35)
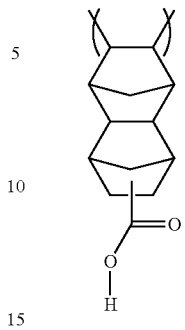

The polymer compound is synthesized by a known method or methods disclosed in the non-patent references.

Examples of a method for introducing an acid dissociable, dissolution inhibiting group (ii) by replacing a hydrogen atom of an alkali soluble group (i) in a precursor include a following method: synthesizing a halogenated methylether compound by using an alcohol compound containing a halogen atom such as chlorine or bromine; and reacting this halogenated methylether compound with an alkali soluble group (i) in a precursor so as to introduce an acid dissociable, dissolution inhibiting group (ii). A detailed method is as follows: reacting a chloromethylether compound, which is a starting material, with any one alkali soluble group (i) selected from an alcoholic hydroxyl group, a carboxyl group, or a phenolic hydroxyl group in a precursor. Thus, the alkali soluble group (i) can be protected by an acid dissociable, dissolution inhibiting group (ii) represented by the general formula (1).

The chloromethylether compound can be synthesized by a known method represented by the following reaction formula. In other words, the desired chloromethylether compound can be obtained as follows: adding paraformaldehyde to an alcohol compound; injecting a hydrogen chloride gas at 2.0 to 3.0 equivalent amount per this alcohol compound; conducting the reaction at a temperature of 40° C. to 100° C. under acid conditions due to hydrochloric acid; and conducting distillation under reduced pressure of the product after completion of the reaction. In the following reaction formula, R corresponds to a group represented by "—$(CH_2)_n$—$R_1$" in a desired compound.

Examples of the chloromethylether compound include 4-oxo-2-adamanthyl chloromethyl ether represented by the following chemical formula (36), 2-adamanthyl chloromethyl ether represented by the following chemical formula (37), and 1-adamanthyl chloromethyl ether represented by the following chemical formula (38).

(36)
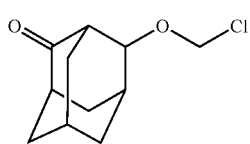

-continued

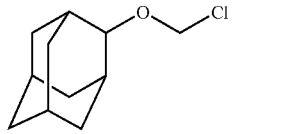

(37)

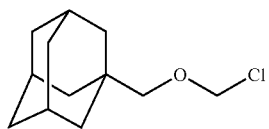

(38)

A polymer compound of the present invention, which is derived from a precursor containing a phenolic hydroxyl group as an alkali soluble group (i), can be obtained by reacting a poly-(α-methyl)hydroxystyrene resin with the halogenated methylether compound, for example.

A polymer compound of the present invention, which is derived from a precursor containing a carboxyl group as an alkali soluble group (i), can be obtained by the following method, for example: reacting the halogenated methylether compound with an unsaturated carboxylic acid such as acrylic acid or methacrylic acid; and polymerizing the obtained unsaturated carboxylate.

An acid dissociable, dissolution inhibiting group (ii) can be introduced into an alkali soluble group (i) by reacting the halogenated methylether compound or another compound containing a cycloaliphatic group with a structural unit containing an alkali soluble group (i) represented by the chemical formulae (21) to (35) or a compound from which this structural unit is derived. Furthermore, a polymer compound of the present invention can be obtained by polymerizing the obtained structural units or compounds from which the structural units are derived, if necessary.

Also, a novel compound (low molecular weight compound) of the present invention can be produced by reacting acrylic acid, which may contain a substituent group ($R_2$), with the halogenated methylether compound. The introduction of a substituent group ($R_2$) can be performed by an optional process.

[Photoresist Composition]

A photoresist composition of the present invention includes at least a base material resin component (A) which exhibits changed alkali solubility under the action of an acid; and an acid generator component (B) which generates the acid on exposure to radiation. Furthermore, the base material resin component (A) is the aforementioned polymer compound of the present invention.

A photoresist composition of the present invention can be positive or negative as far as it includes the above characteristics.

In the case of a negative photoresist composition, an alkali soluble resin is used as a component (A), and the alkali soluble resin is blended with a cross-linking agent. When an acid is generated from a component (B) on exposure during formation of a resist pattern, a cross-linkage occurs between an alkali soluble resin and the cross-linking agent under the action of the acid. Then, an alkali soluble resin is changed to be alkali insoluble. Examples of the cross-linking agent include an amino-type cross-linking agent such as a melamine containing a methylol group or an alkoxymethyl group, urea, or glycoluril.

In the case of a positive photoresist composition, a component (A) includes an alkali insoluble structural unit containing an acid dissociable, dissolution inhibiting group (ii). An acid dissociable, dissolution inhibiting group (ii) is dissociated under the action of an acid which is generated from a component (B) on exposure. Then, a whole component (A) is changed from being alkali insoluble to being alkali soluble. Accordingly, when exposure through a mask pattern, or this exposure followed by post exposure baking (PEB) are performed during formation of a resist pattern, an exposed part is changed to alkali soluble, whereas an unexposed part remains alkali insoluble without change. Therefore, a positive resist pattern can be formed by alkali development. In the case of a positive photoresist composition, a polymer compound of the present invention is used as a component (A).

When a polymer compound containing a phenolic hydroxyl group as an alkali soluble group (i) is used as a precursor in the base material resin component (A), a ratio of a structural unit containing an alkali soluble group (i) to all structural units constituting the component (A) is preferably 50 to 95 mol %, more preferably 55 to 90 mol %, and most preferably 65 to 90 mol %. Meanwhile, the ratio of a structural unit protected by an acid dissociable, dissolution inhibiting group (ii) is preferably 3 to 50 mol %, more preferably 7 to 30 mol %, and most preferably 10 to 25 mol %.

When a polymer compound containing an alcoholic hydroxyl group as an alkali soluble group (i) is used as a precursor in the base material resin component (A), a ratio of a structural unit containing an alkali soluble group (i) to all structural units constituting the component (A) is preferably 50 to 95 mol %, more preferably 55 to 90 mol %, and most preferably 55 to 85 mol %. Meanwhile, the ratio of a structural unit protected by an acid dissociable, dissolution inhibiting group (ii) is preferably 3 to 50 mol %, more preferably 5 to 35 mol %, and most preferably 7 to 25 mol %.

[Structural Unit (a1)]

When a polymer compound containing a carboxyl group as an alkali soluble group (i) is used as a precursor in the base material resin component (A), it is preferable that a structural unit (a1) derived from a compound represented by the general formula (2) be used as a structural unit protected by an acid dissociable, dissolution inhibiting group (ii).

In this case, a polymer, which is obtained by copolymerizing the structural unit (a1) and other known structural units generally used in a chemically amplified photoresist composition, can be used as the base material resin component (A). Examples of the other structural units include the following structural units (a2) to (a6). For example, a structural unit forming a cyclic or linear tertiary alkylester with a carboxyl group of (meth)acrylic acid is well-known as the other structural unit.

A structural unit derived from at least one compound selected from a following general formula (39) can be used as a structural unit (a1). Since these structural units contain an acetal group (—R—O—R'; an alkoxyalkyl group), an acid dissociable, dissolution inhibiting group (ii) tends to be easily dissociated under the action of an acid in comparison with a structural unit (a2) described below, for example. Therefore, even an acid generator generating an acid whose acid strength is weak (such as a diazomethane-type acid generator, an oxime sulfonate-type acid generator, or an onium salt containing camphor sulfonic acid in an anion part, each being described below) can dissociate an acid dissociable, dissolution inhibiting group (ii) sufficiently.

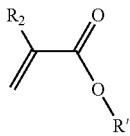
(39)

(wherein R' represents a group represented by the chemical formulae (4) to (15), and $R_2$ represents the same as the aforementioned.)

Among them, it is preferable that a structural unit (a1) be at least one selected from structural units represented by the following chemical formulae (40) to (42).

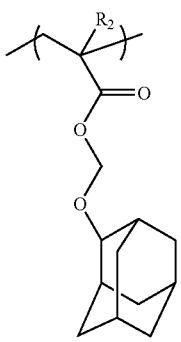
(40)

(wherein $R_2$ represents the same as the aforementioned.)

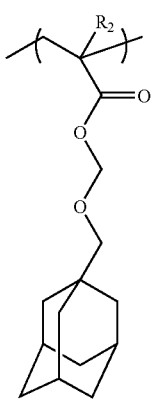
(41)

(wherein $R_2$ represents the same as the aforementioned.)

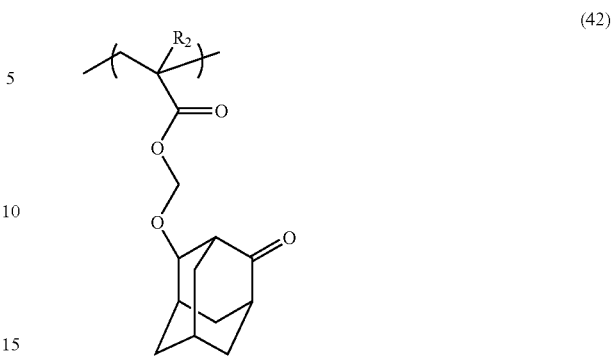
(42)

(wherein $R_2$ represents the same as the aforementioned.)

Line edge roughness is reduced by using a structural unit (a1) represented by any one of the chemical formulae (40) to (42) as a structural unit containing an acid dissociable, dissolution inhibiting group (ii). Also, since even a weak acid can dissociate an acid dissociable, dissolution inhibiting group (ii), various acid generators can be used.

In addition, exposure margin and exposure area margin are improved. Exposure area margin is a problem in that a shape and size of a resist is changed due to the difference of coverage and coordinates in a cell (at which part of a cell of an exposure apparatus a resist is located, a peripheral part or a central part).

An acetal-type protecting group of the present invention has very low deprotection energy and a deprotection reaction can proceed with only exposure energy, thereby it is hardly affected by acid dispersion or deactivation. It is believed that the exposure area margin is improved for these reasons.

In addition, thermal stability is improved because a structural unit (a1) shows a higher heat decomposition point than a tertiary ester compound of (meth)acrylic acid such as structural unit (a2) described below. Accordingly, storage stability is also improved. Moreover, it is possible to perform PEB at low temperature because a structural unit (a1) shows a lower Tg (glass transition point) than a structural unit (a2) described below and dissociates a protecting group during exposure (a structural unit (a2) dissociates a protecting group during PEB). In other words, it is possible to easily control diffusion of an acid generator; therefore, it is possible to easily control a resist pattern shape. In addition, the PEB margin becomes favorable. Also, excellent resolution and a favorable shape of a resist pattern can be provided even in an inorganic substrate such as a SiON substrate.

A component (A) of a photoresist composition of the present invention can include a structural unit (a2) described below as a structural unit containing an acid dissociable, dissolution inhibiting group (ii), although the ratio of the structural unit (a1) in a component (A) is preferably 50% by mass or more, more preferably 80% by mass, and most preferably 100% by mass.

[Structural Unit (a2)]

A structural unit (a2) is a structural unit derived from a (meth)acrylate containing a monocyclic or polycyclic group-containing acid dissociable, dissolution inhibiting group, and examples thereof include a structural unit containing an acid dissociable, dissolution inhibiting group other than a structural unit (a1). These can be used in an amount range that does not deteriorate the effect of the present invention.

Examples of a monocyclic group include a group in which one hydrogen atom is removed from a cycloalkane, for example an aliphatic monocyclic group such as a cyclohexyl group or a cyclopentyl group. Examples of a polycyclic group include a group in which one hydrogen atom is removed from a polycycloalkane such as adamantane, norbornane, isobornane, tricyclodecane, or tetracyclododecane which is a bicycloalkane, a tricycloalkane, or a tetracycloalkane. In other words, an aliphatic polycyclic group can be cited. Herein, these monocyclic or polycyclic groups have been proposed in an ArF resist. In the present invention, it is possible to optionally select and use one from these monocyclic or polycyclic groups. Among them, an aliphatic polycyclic group such as an adamantyl group, a norbornyl group, or a tetracyclododecanyl group is preferable because they are easily available industrially. In detail, at least one structural unit selected from the following general formula (43), (44), or (45) is preferable because they are excellent in resolution, dry etching resistance, and so on.

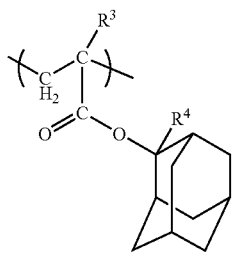

(43)

(wherein $R^3$ represents a hydrogen atom or a lower alkyl group, and $R^4$ represents a lower alkyl group.)

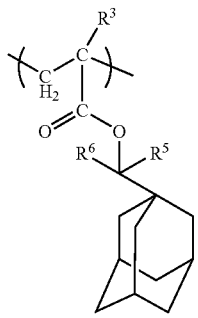

(44)

(wherein $R^3$ represents a hydrogen atom or a lower alkyl group, and $R^5$ and $R^6$ independently represents a lower alkyl group.)

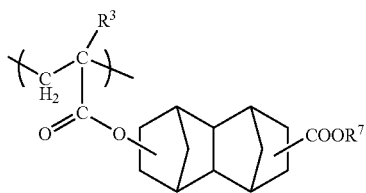

(45)

(wherein $R^3$ represents a hydrogen atom or a lower alkyl group, and $R^7$ represents a tertiary alkyl group.)

In a structural unit represented by the general formula (43), a carbon atom adjacent to the oxygen atom (—O—) in an ester part of (meth)acrylic acid is a tertiary carbon in a ring backbone such as an adamantyl group which is a tertiary alkyl group.

Examples of $R^3$ include a hydrogen atom, a methyl group, and a lower alkyl group containing about 2 to 5 carbon atoms, specifically a linear or branched, lower alkyl group such as an ethyl group, a propyl group, an isopropyl group, an n-butyl group, an isobutyl group, a tert-butyl group, a pentyl group, an isopentyl group, or a neopentyl group.

Also, examples of $R^4$ include a lower alkyl group containing about 1 to 5 carbon atoms, specifically a linear or branched, lower alkyl group such as a methyl group, an ethyl group, a propyl group, an isopropyl group, an n-butyl group, an isobutyl group, a tert-butyl group, a pentyl group, an isopentyl group, or a neopentyl group. Herein, it is preferable that $R^4$ represent an alkyl group containing no less than 2 carbon atoms because they tend to have a higher acid dissociability than a methyl group. However, a methyl group and an ethyl group are most preferable industrially.

In a structural unit represented by a general formula (44), a carbon atom adjacent to the oxygen atom (—O—) in an ester part of (meth)acrylic acid is a tertiary carbon in a tertiary alkyl group in which a ring backbone such as an adamantyl group exists. $R^3$ represents the same as in the general formula (43), and $R^5$ and $R^6$ independently represents a lower alkyl group that is the aforementioned linear or branched alkyl group containing about 1 to 5 carbon atoms. These groups tend to have a higher acid dissociability than a 2-methyl-2-adamantyl group. Herein, it is industrially preferable that both of $R^5$ and $R^6$ represent a methyl group.

In a structural unit represented by a general formula (45), a carbon atom adjacent to the oxygen atom (—O—) in another ester part than the ester part of (meth)acrylic acid is a tertiary carbon in a tertiary alkyl group, and the other ester part and the ester part of (meth)acrylic acid is linked through a ring backbone such as a tetracyclododecanyl group. In a structural unit represented by the general formula (45), $R^3$ represents the same as in the general formula (43), $R^7$ represents a tertiary alkyl group such as a tert-butyl group or a tert-amyl group, preferably a tertiary alkyl group containing about 4 to 5 carbon atoms. Herein, it is industrially preferable that $R^7$ represent a tert-butyl group.

Also, among these structural units represented by the general formulae (43) to (45), the structural unit represented by the general formulae (43), in which $R^4$ represents a methyl group or an ethyl group, is preferable because it is excellent in resolution.

[Structural Unit (a3)]

A structural unit (a3) is a structural unit derived from (meth)acrylate containing a lactone-containing monocyclic or polycyclic group. A lactone functional group is useful for improving the following characteristics of a photoresist film formed of a photoresist composition of the present invention: the adhesion to a substrate and the affinity to a developing solution.

Herein, a lactone ring means one ring containing a structure of —O—C(O)—, and the ring is counted as a first ring. Accordingly, a group containing only a lactone ring is referred to as a monocyclic group, and a group containing other cyclic structures in addition to a lactone ring is referred to as a polycyclic group regardless of their structures.

As a structural unit (a3), any structural unit can be used without any particular limitation as long as it contains both a lactone functional group and a cyclic group. In detail, examples of a lactone-containing monocyclic group include a group in which one hydrogen atom is removed from γ-butyrolactone, and examples of a lactone-containing polycyclic group include a group in which one hydrogen atom is removed from a bicycloalkane, a tricycloalkane, or a tetracycloalkane, each containing a lactone group. In particular, a group in which one hydrogen atom is removed from a lactone-containing tricycloalkane represented by the following structural formula (46) or (47) is preferable because it is easily available industrially.

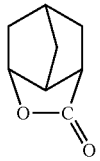
(46)

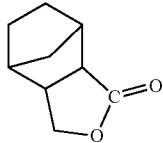
(47)

Also, specific examples of a structural unit (a3) include a structural unit derived from (meth)acrylate containing a lactone-containing monocycloalkyl or tricycloalkyl group, and more specific examples include a structural unit represented by the following general formulae (48) to (50).

(48)

(49)

(wherein R³ represents a hydrogen atom or a lower alkyl group.)

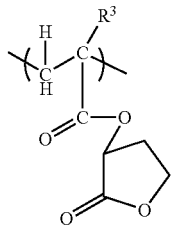
(50)

(wherein R³ represents a hydrogen atom or a lower alkyl group.)

Examples of R³ include a hydrogen atom, a methyl group, and a lower alkyl group containing about 2 to 5 carbon atoms, specifically a linear or branched, lower alkyl group such as an ethyl group, a propyl group, an isopropyl group, an n-butyl group, an isobutyl group, a tert-butyl group, a pentyl group, an isopentyl group, or a neopentyl group.

Among these structural units represented by general formulae (48) to (50), a structural unit derived from γ-butyrolactone ester of (meth)acrylic acid containing an ester bond at α-carbon, namely (meth)acrylate of γ-butyrolactone, as represented by the general formula (50) is preferable because it is excellent in the inhibition and reduction effects against a proximity effect.

Also, a structural unit derived from norbornane-lactone ester of (meth)acrylic acid, namely (meth)acrylate of norbornane-lactone, as represented by the general formula (48) or (49) is preferable because it has a favorable shape of an obtained resist pattern, for example rectangularity. In particular, a structural unit represented by the formula (49) is preferable because the above effect is quite high.

The structural unit (a3) can be used alone or in combination of two or more being different from each other. The adhesion to a substrate, the affinity to an alkali developing solution, and the etching resistance of a photoresist film are further improved by introducing two or more lactone backbones being different from each other into a resin backbone. Preferable examples of the combination of lactones include a combination of a monocyclic lactone and a polycyclic lactone. Also, a combination of a structural unit derived from (meth)acrylate of γ-butyrolactone as represented by the general formula (50) and a structural unit derived from (meth) acrylate of norbornane-lactone as represented by the general formula (48) or (49) is most preferable because etching resistance and adhesion to a substrate are improved.

[Structural Unit (a4)]

A structural unit (a4) is a structural unit derived from (meth)acrylate containing a polar group-containing polycyclic group. By containing a polar group, a structural unit (a4) can improve the affinity of all the resin component (A) to an alkali developing solution and the alkali solubility in an exposed part, thereby contributing to improving resolution. Herein, as a polycyclic group, the same polycyclic group can be used as in the structural unit (a1). Examples of the polar group include a cyano group, a carboxyl group, and a hydroxyl group, and a hydroxyl group is preferable.

As a structural unit (a4), any structural unit can be used without any particular limitation, as long as it contains a polar group-containing polycyclic group. In detail, a structural unit containing a hydroxyl group-containing adamantyl group, particularly a structural unit represented by a following general formula (51) is preferable because it possesses the effects of improving dry etching resistance and making a cross-sectional surface of a pattern rectangular.

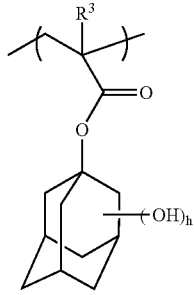

(51)

(wherein R³ represents the same as the aforementioned, h represents an integer of 1 to 3.)

Among them, a structural unit is preferable, in which h represents 1, and a hydroxyl group is bonded to the 3rd position of an adamantyl group.

[Structural Unit (a5)]

A structural unit (a5) is a structural unit derived from (meth)acrylate containing a polycyclic group-containing, non-acid dissociable, dissolution inhibiting group other than the structural units (a1) to (a4).

A structural unit derived from (meth)acrylate containing a polycyclic group-containing, non-acid dissociable, dissolution inhibiting group means a structural unit capable of enhancing the hydrophobicity of all the component (A) before and after exposure, thereby inhibiting alkali solubility. In other words, the structural unit (a5) is a structural unit containing a group which reduces alkali solubility of all the component (A) before exposure, which is not dissociated under the action of an acid generated from a component (B) after exposure, and which possesses a dissolution inhibiting property reducing alkali solubility of all the component (A) as long as it does not become alkali insoluble when it is changed to alkali soluble by dissociating an acid dissociable, dissolution inhibiting group (ii) of the structural unit (a1) or (a2).

The structural unit (a5) does not overlap the structural units (a1) to (a4). In other words, the structural unit (a5) does not contain any of an acid dissociable, dissolution inhibiting group (ii) in the structural units (a1) and (a2), a lactone group in the structural unit (a3), and a polar group in the structural unit (a4).

As a polycyclic group in the structural unit (as), the same polycyclic group can be used as in the structural unit (a2).

As a structural unit (a5), many structural units can be used, which are conventionally known as an ArF positive resist material. In particular, a structural unit derived from at least one selected from tricyclodecanyl (meth)acrylate, adamantyl (meth)acrylate, tetracyclododecanyl (meth)acrylate, or isobornyl (meth)acrylate because it is easily available industrially. These examples of a structural unit (as) are represented by following general formulae (52) to (54). Among them, a structural unit represented by the general formula (52) is preferable because a shape of an obtained resist pattern such as rectangularity is particularly favorable.

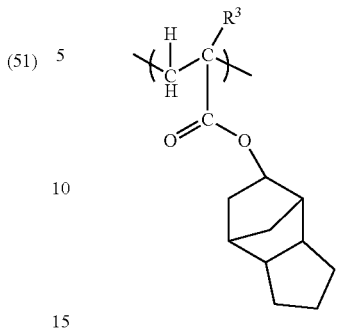

(52)

(wherein R³ represents a hydrogen atom or a lower alkyl group.)

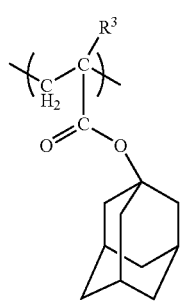

(53)

(wherein R³ represents a hydrogen atom or a lower alkyl group.)

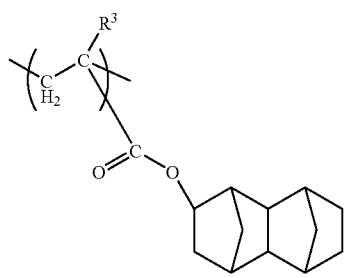

(54)

(wherein R³ represents a hydrogen atom or a lower alkyl group.)

Examples of R³ include a hydrogen atom, a methyl group, and a lower alkyl group containing about 2 to 5 carbon atoms, specifically a linear or branched, lower alkyl group such as an ethyl group, a propyl group, an isopropyl group, an n-butyl group, an isobutyl group, a tert-butyl group, a pentyl group, an isopentyl group, or a neopentyl group.

[Structural Unit (a6)]

A structural unit (a6) is a structural unit which does not overlap the structural units (a1) to (a5), which is represented by a following general formula (55), and which is derived from a compound containing a cyclic group X' bonded to acrylate which may contain a substituent group and a fluorinated organic group bonded to the cyclic group X'. The fluorinated organic group is formed by replacing at least one hydrogen atom of an organic group with fluorine and contains an alcoholic hydroxyl group. When a base material resin component (A) includes the structural unit (a6), alkali solubility is improved. In addition, resolution is improved due to the enhancement of dissolution contrast.

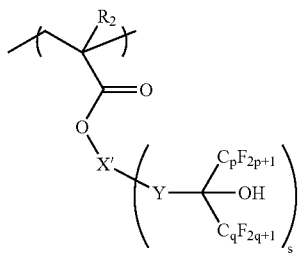

(55)

R$_2$ represents the same as the aforementioned, X' represents a divalent or trivalent cyclic group, Y represents an alkylene or alkyleneoxy group containing 1 to 6 carbon atoms which is divalent, p and q independently represent an integer of 1 to 5, and represents an integer of 1 or 2.

In the general formula (55), as a divalent or trivalent cyclic group represented by X', any group can be used without any particular limitation as long as it is a cyclic group, and examples thereof include aliphatic and aromatic cyclic groups. Among them, an aromatic cyclic group can be used in a photoresist composition for KrF exposure. In particular, it is preferable that an aliphatic cyclic group be used in a photoresist composition for ArF exposure because the transparency of a photoresist film is improved.

When X' is divalent, s represents 1. When X' is trivalent, s represents 2. In other words, when X' is trivalent, two fluorinated organic groups are bonded to X'.

As an aromatic cyclic group, various aromatic monocyclic or polycyclic groups which are divalent or trivalent can be used without any particular limitation. Examples thereof include a group in which two or three hydrogen atoms are removed from an aromatic hydrocarbon, and examples of the aromatic hydrocarbon include benzene, naphthalene, and anthracene.

As an aliphatic cyclic group, various aliphatic monocyclic or polycyclic groups which are divalent or trivalent can be used without any particular limitation. Examples of the aliphatic cyclic group include a group in which two or three hydrogen atoms are removed from an aliphatic cyclic hydrocarbon, and examples of the aliphatic cyclic hydrocarbon include an aliphatic monocyclic hydrocarbon such as cyclohexane or cyclopentane and an aliphatic polycyclic hydrocarbon. The groups in which two or three hydrogen atoms are removed from these hydrocarbons can be used as an aliphatic cyclic group.

Among them, an aliphatic polycyclic hydrocarbon is more preferable, and examples thereof include adamantane, norbornane, norbornene, methylnorbornane, ethylnorbornane, methylnorbornene, ethylnorbornene, isobornane, tricyclodecane, or tetracyclododecane. The aliphatic polycyclic hydrocarbon can be appropriately selected and used from among many cycloaliphatic groups having been proposed in an ArF resist. Among them, adamantane, norbornane, norbornene, methylnorbornane, ethylnorbornane, methylnorbornene, ethylnorbornene, or tetracyclododecane is preferable industrially, and norbornane is most preferable.

Y represents an alkylene or alkyleneoxy group containing 1 to 6 carbon atoms which is divalent, and there is no particular limitation although a methylene group is preferable. It is preferable that each of p, q, and s represent 1.

Among them, a compound represented by a following general formula (56) is most preferable.

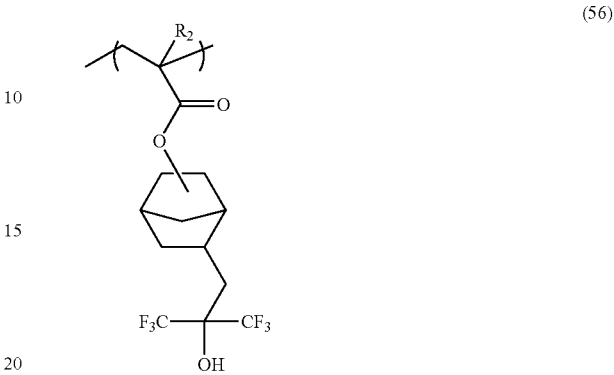

(56)

(wherein R$_2$ represents the same as the aforementioned.)

[Other Structural Units]

Also, in a positive photoresist composition of the present invention, a copolymer can be used as the component (A), which is formed by appropriately combining structural units derived from: (meth)acrylic acid derivative containing a dry etching resistance-enhancing group or non-acid dissociable, dissolution inhibiting group, which is known as a conventional, chemically amplified positive resist; carboxylic acid containing an ethylenic double bond for enhancing alkali solubility, such as (meth)acrylic acid, maleic acid, or fumaric acid; and a known monomer used for producing an acryl resin.

Examples of the acrylic acid derivative include acrylate, in which a hydroxyl group of a carboxyl group is protected by a dry etching resistance-enhancing group or non-acid dissociable, dissolution inhibiting group, such as naphthyl acrylate, benzyl acrylate, 3-oxocyclohexyl acrylate, an ester of acrylic acid and terpineol, or an ester of acrylic acid and 3-bromoacetone. Also, examples of the methacrylic acid derivative include a methacrylic acid derivative corresponding to the aforementioned acrylic acid derivative.

Also, examples of the carboxylic acid containing an ethylenic double bond include acrylic acid, methacrylic acid, maleic acid, and fumaric acid.

Examples of a known monomer used for producing an acrylic resin include an alkyl acrylate such as methyl acrylate, ethyl acrylate, propyl acrylate, isopropyl acrylate, n-butyl acrylate, isobutyl acrylate, n-hexyl acrylate, octyl acrylate, 2-etylhexyl acrylate, lauryl acrylate, 2-hydroxyethyl acrylate, or 2-hydroxypropyl acrylate; and a methacrylate corresponding to the alkylacrylate.

[Polymer Compound Including Structural Unit (a1)]

As a polymer compound which is preferable as the base material resin component (A) used in a positive resist composition of the present invention, a copolymer including structural units (a1) and (a3) is preferable because the resolution and the shape of a resist pattern become favorable. In particular, a polymer compound including structural units (a1), (a3), and (a4) is more preferable. Also, a polymer compound including two mutually different structural units (a3) in the base material resin is preferable.

When a polymer compound of the present invention is used in a binary system (a copolymer of structural units (a1) and (a3)), the proportion of the structural unit (a1) is 20 to 80 mol %, preferably 30 to 60 mol % per the sum of all structural units of the component (A), and the proportion of the structural unit (a3) is 20 to 80 mol %, preferably 30 to 60 mol %.

When a polymer compound of the present invention is used in a binary system (a copolymer of structural units (a1) and (a6)), the proportion of the structural unit (a1) is 20 to 80 mol %, preferably 30 to 60 mol % per the sum of all structural units of the component (A), and the proportion of the structural unit (a6) is 20 to 80 mol %, preferably 30 to 60 mol %. When a polymer compound of the present invention is used in a ternary system (a copolymer of structural units (a1), (a3), and (a4)), the proportion of the structural unit (a1) is 20 to 60 mol %, preferably 30 to 50 mol % per the sum of all structural units of the component (A), the proportion of the structural unit (a3) is 20 to 60 mol %, preferably 20 to 50 mol %, and the proportion of the structural unit (a4) is 10 to 50 mol %, preferably 20 to 40 mol %. When the proportions of all structural units in the component (A) are within the aforementioned ranges, it is possible to obtain a positive resist composition excellent in resolution and dry etching resistance.

When a polymer compound of the present invention is used in a quaternary system (a copolymer of structural units (a1), (a3), (a4), and (a5)), the proportion of the structural unit (a1) is 25 to 50 mol %, preferably 30 to 40 mol % per the sum of all structural units of the component (A), the proportion of the structural unit (a3) is 25 to 50 mol %, preferably 30 to 40 mol %, the proportion of the structural unit (a4) is 10 to 30 mol %, preferably 10 to 20 mol %, and the proportion of the structural unit (a5) is 3 to 25 mol %, preferably 5 to 20 mol %. When the proportions of all structural units in the component (A) are within the aforementioned ranges, it is possible to markedly improve depth of focus of an isolated pattern formed of an obtained positive resist composition and to sufficiently inhibit and reduce a proximity effect, thereby improving resolution.

The copolymers of structural units (a1) and (a3); structural units (a1) and (a6); structural units (a1), (a3), and (a4); structural units (a1), (a3), (a4), and (a5) can be copolymerized and used with a structural unit (a2) or other structural units in an amount range that does not deteriorate the effects of the present invention.

The polymer compound including the structural unit (a1) can be obtained by copolymerizing monomers, from which structural units are derived, according to a known radical polymerization method or the like using a radical polymerization initiator such as azobisisobutylonitrile (AIBN).

An amount of the base material component (A) in a photoresist composition of the present invention can be adjusted according to a desired thickness of a resist film to be formed. For example, this amount is adjusted to provide a preferable concentration of a solid part described below.

Also, a —C(CF$_3$)$_2$—OH group can be introduced into an end of the polymer compound by simultaneously using a chain transfer agent such as HS—CH$_2$—CH$_2$—CH$_2$—C(CF$_3$)$_2$—OH during the aforementioned polymerization.

A copolymer containing a hydroxylalkyl group, in which at least one hydrogen atom of an alkyl group is substituted by a fluorine atom, is excellent in the reduction of a developing defect and LER (line edge roughness: unevenness of line side wall).

[Component (B)]

A suitable acid generator component (B) used in a photoresist composition of the present invention can be selected from among known compounds which generate an acid on exposure to radiation. Examples of the acid generator (B) include an onium salt-type acid generator such as an iodonium salt or a sulfonium salt; an oxime sulfonate-type acid generator; a diazomethane-type acid generator such as bisalkyl- or bisaryl-sulfonyldiazomethanes, poly(bissulfonyl) diazomethanes, or diazomethanenitrobenzylsulfonates; an iminosulfonate-type acid generator; and a disulfonic acid-type acid generator.

Specific examples of the onium salt-type acid generator include trifluoromethanesulfonate or nonafluorobutanesulfonate of diphenyliodonium; trifluoromethanesulfonate or nonafluorobutanesulfonate of bis(4-tert-butylphenyl)iodonium; trifluoromethanesulfonate, heptafluoropropanesulfonate, or nonafluorobutanesulfonate of triphenylsulfonium; trifluoromethanesulfonate, heptafluoropropanesulfonate, or nonafluorobutanesulfonate of tri(4-methylphenyl)sulfonium; trifluoromethanesulfonate, heptafluoropropanesulfonate, or nonafluorobutanesulfonate of dimethyl(4-hydroxynaphtyl)sulfonium; trifluoromethanesulfonate, heptafluoropropanesulfonate, or nonafluorobutanesulfonate of monophenyldimethylsulfonium; and trifluoromethanesulfonate, heptafluoropropanesulfonate, or nonafluorobutanesulfonate of diphenylmonomethylsulfonium. Among them, an onium salt containing an anion of fluorinated alkyl sulfonic acid ion is preferable.

Even an onium salt containing a camphor sulfonic acid ion in an anion part, whose acid strength is weak, can be used among the onium salt-type acid generators. Specific examples can include the compound represented by the following chemical formula (57).

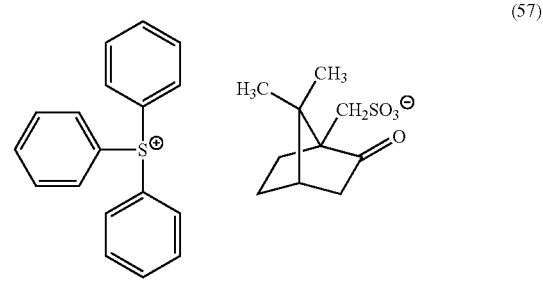

(57)

Specific examples of the oxime sulfonate type acid generator include α-(methylsulfonyloxyimino)-phenylacetonitrile, α-(methylsulfonyloxyimino)-p-methoxyphenylacetonitrile, α-(trifluoromethylsulfonyloxyimino)-phenylacetonitrile, α-(trifluoromethylsulfonyloxyimino)-p-methoxyphenylacetonitrile, α-(ethylsulfonyloxyimino)-p-methoxyphenylacetonitrile, α-(propylsulfonyloxyimino)-p-methylphenylacetonitrile, and α-(methylsulfonyloxyimino)-p-bromophenylacetonitrile. Among them α-(methylsulfonyloxyimino)-p-methoxyphenylacetonitrile is preferable.

Specific examples of the bis(alkylsulfonyl)- or bis(arylsulfonyl)-diazomethanes of the diazomethane-type acid generator include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, bis(2,4-dimethylphenylsulfonyl)diazomethane.

Also, specific examples of the poly(bissulfonyl)diazomethanes include 1,3-bis(phenylsulfonyldiazomethylsulfonyl)propane (compound A, decomposition point 135° C.), 1,4-bis(phenylsulfonyldiazomethylsulfonyl)butane (compound B, decomposition point 147° C.), 1,6-bis(phenylsulfonyldiazomethylsulfonyl)hexane (compound C, melting point 132° C., decomposition point 145° C.), 1,10-bis(phenylsulfonyldiazomethylsulfonyl)decane (compound D, decomposition point 147° C.), 1,2-bis(cyclohexylsulfonyldiazomethylsulfonyl)ethane (compound E, decomposition point 149° C.), 1,3-bis(cyclohexylsulfonyldiazomethylsulfonyl)propane (compound F, decomposition point 153° C.), 1,6-bis(cyclohexylsulfonyldiazomethylsulfonyl)hexane (compound G, melting point 109° C., decomposition point 122° C.), 1,10-bis(cyclohexylsulfonyldiazomethylsulfonyl)decane (compound H, decomposition point 116° C.).

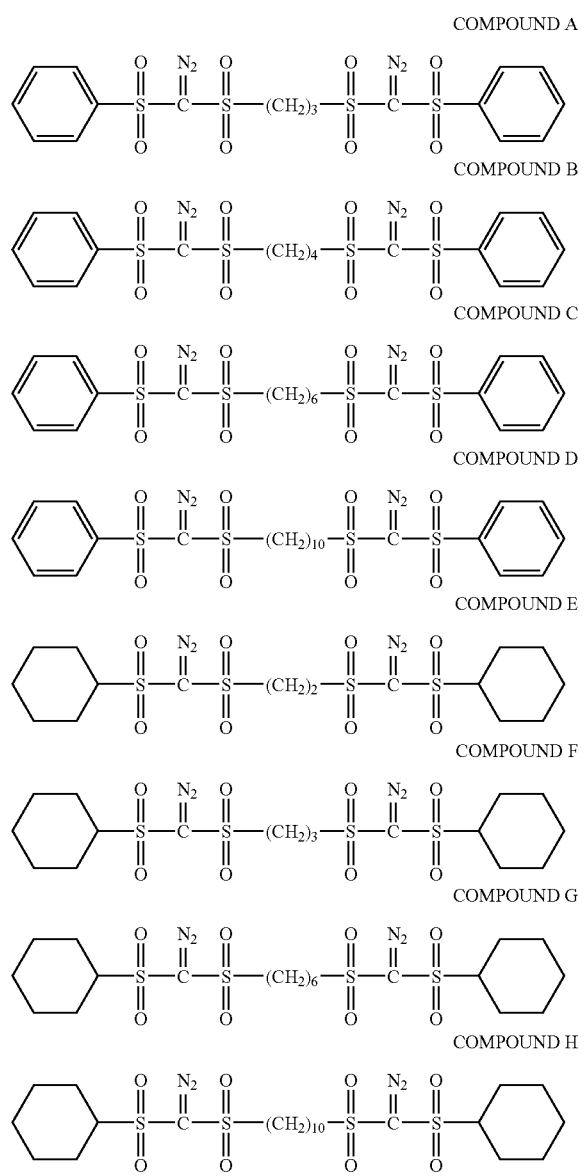

COMPOUND A

COMPOUND B

COMPOUND C

COMPOUND D

COMPOUND E

COMPOUND F

COMPOUND G

COMPOUND H

An acid generator (B) can be used alone or in combination of two or more.

The content of an acid generator (B) is 0.5 to 30 parts by mass per 100 parts by mass of the component (A), preferably 1 to 15 parts by mass, more preferably 3 to 10 parts by mass. When the content of an acid generator (B) is within the above range, it is possible to obtain a homogeneous solution, to improve storage stability, and to perform pattern formation sufficiently.

[Component (D)]

The photoresist composition can further include a nitrogen-containing organic compound (D) according to need. It is generally known that a small amount of a nitrogen-containing organic compound can be added to a chemically amplified resist composition as an acid diffusion inhibitor. In the present invention, a generally known nitrogen-containing organic compound can be added to the photoresist composition. Examples of the nitrogen-containing organic compound include an amine and an ammonium salt.

Examples of the amine include an aliphatic secondary amine such as diethylamine, dipropylamine, dibutylamine, or dipentylamine; an aliphatic tertiary amine (a trialkylamine in which three alkyl groups bonded to nitrogen can be the same or different) such as trimethylamine, triethylamine, tripropylamine, tributylamine, tripentylamine, N,N-dimethylpropylamine, N-ethyl-N-methylbutylamine, trihexylamine, triheptylamine, trioctylamin, tridecanylamine, tridodecanylamine, or tritetradecanylamine; a tertiary alkanolamine such as N,N-dimethylmonoethanolamine, triisopropanolamine, N,N-diethylmonoethanolamine, triethanolamine, or tributanolamine; an aromatic tertiary amine such as N,N-dimethylaniline, N,N-diethylaniline, N-ethyl-N-methylaniline, N,N-dimethyltoluidine, N-methyldiphenylamine, N-ethyldiphenylamine, or triphenylamine.

Examples of the ammonium salt include salts of a quaternary alkylammonium ion such as an ammonium ion, a tetramethylammonium ion, a tetraethylammonium ion, a tetrapropylammonium ion, a tetrabutylammonium ion, or a tetrapentylammonium ion; and a hydroxyl group-containing organic carboxylic acid such as lactic acid.

Among them, preferable examples include a lower tertiary alkanolamine such as triethanolamine, triisopropanolamine, or tributanolamine; and a trialkylamine containing 6 to 15 carbon atoms such as trihexylamine, triheptylamine, trioctylamine, tridecanylamine, tridodecanylamine, or tritetradecanylamine because these are excellent in reducing thickness loss in the top part of a fine resist pattern.

A nitrogen-containing organic compound (D) can be used in a range of usually 0.01 to 5 parts by mass per 100 parts by mass of the base material component (A), preferably 0.05 to 3 parts, more preferably 0.1 to 2 parts by mass. When the content of a component (D) is within the above range, it is possible to obtain an improvement in a pattern shape due to a diffusion inhibiting effect of an acid generated on exposure and to prevent a so-called deterioration of exposure sensitivity due to an excessive inhibition of acid diffusion.

[Acid Component]

Also, a photoresist composition of the present invention can further include an organic carboxylic acid, or an oxoacid of phosphorous or a derivative thereof as an optional component for the purpose of preventing the deterioration of sensitivity due to the addition of the nitrogen-containing organic compound (D).

Preferable examples of the organic carboxylic acid include malonic acid, citric acid, malic acid, succinic acid, benzoic acid, and salicylic acid.

Examples of the oxoacid of phosphorous or the derivative thereof include phosphoric acid or an ester derivative thereof such as phosphoric acid, di-n-butyl phosphate, or diphenyl phosphate; phosphonic acid or an ester derivative thereof such as phosphonic acid, dimethyl phosphonate, di-n-butyl phosphonate, phenylphosphonic acid, diphenyl phosphonate, or dibenzyl phosphonate; and phosphinic acid or an ester derivative thereof such as phosphinic acid or phenylphosphinic acid, although phosphonic acid is particularly preferable among them. The organic carboxylic acid, or the oxoacid of phosphorous or the derivative thereof can be used in a range of 0.01 to 5.0 parts by mass per 100 parts by mass of the base material component (A), preferably 0.05 to 3 parts, more preferably 0.1 to 2 parts by mass.

[Organic Solvent (E)]

The photoresist composition of the present invention can be produced by dissolving the base material resin component (A), the acid generator (B), the nitrogen-containing organic compound (D), and optional components according to need in an organic solvent (E) to be a homogeneous solution. One, or two or more organic solvents (E) can be selected to be used from among known solvents for a chemically amplified resist.

Examples of the organic solvent (E) include ketones such as γ-butyrolactone, acetone, methyl ethyl ketone, cyclohexanone, methyl isoamyl ketone, or 2-heptanone; polyhydric alcohols and derivatives thereof such as ethylene glycol, ethylene glycol monoacetate, diethylene glycol, diethylene glycol monoacetate, propylene glycol, propylene glycol monoacetate, dipropylene glycol, or the monomethyl ether, monoethyl ether, monopropyl ether, monobutyl ether, or monophenyl ether of dipropylene glycol monoacetate; cyclic ethers such as dioxane; and esters such as methyl lactate, ethyl lactate, methyl acetate, ethyl acetate, butyl acetate, methyl pyruvate, ethyl pyruvate, methyl methoxypropionate, or ethyl ethoxypropionate. These organic solvents can be used alone, or in a mixed solvent of two or more different solvents. In particular, the mixed solvent of propylene glycol monomethyl ether acetate (PGMEA) and a polar solvent is preferable, and the mixture ratio can be appropriately determined in consideration of miscibility of PGMEA and a polar solvent although the mass ratio of PGMEA:(polar solvent) is preferably within a range of 1:9 to 9:1, more preferably 2:8 to 8:2.

Specifically, in the case of blending ethyl lactate (EL) as a polar solvent, the mass ratio of PGMEA:EA is preferably 2:8 to 8:2, more preferably 3:7 to 7:3. Also, the mixed solvent of γ-butyrolactone and at least one selected from PGMEA and EL is preferable as an organic solvent (E). In this case, as for the mixture ratio, the mass ratio of the former and the latter is preferably 70:30 to 95:5. The amount of a component (E) is not specifically limited and is appropriately determined according to the thickness of a coating film and the concentration capable of coating on a substrate. Generally, the concentration of a solid part of a photoresist composition is 2 to 20 mass %, preferably 5 to 15 mass %, and more preferably 5 to 12 mass %.

[Other Components]

Also, a photoresist composition of the present invention can further include miscible additives such as generally known dissolution inhibitors, additive resins for improving properties of a photoresist film, surfactants for improving coating property, plasticizers, stabilizers, colorants, and halation prevention agents according to need.

Also, a compound containing an alcoholic hydroxyl group, a phenolic hydroxyl group, or a carboxyl group, each being protected by an acid dissociable, dissolution inhibiting group (ii) of the present invention, can be used as a dissolution inhibitor. Preferable examples of the dissolution inhibitor include a compound in which an acid dissociable, dissolution inhibiting group (ii) of the present invention protects an alkali soluble group (i), particularly an alcoholic hydroxyl group, a phenolic hydroxyl group, or a carboxyl group, in monomer components corresponding to the structural units represented by the chemical formulae (21) to (35). In a photoresist composition including the aforementioned compound as an acid dissociable, dissolution inhibitor (C) with the base material resin (A), a dissolution inhibiting effect in an alkali development is shown before exposure, whereas alkali solubility due to deprotection is shown after exposure. Therefore, it is possible to prevent thickness loss of a resist pattern and to provide a fine pattern with high resolution.

In particular, a compound of the present invention contains an acid dissociable, dissolution inhibiting group containing a cycloaliphatic group in this molecule; therefore, the alkali solubility is greatly changed under the action of an acid. Accordingly, according to a polymer compound of the present invention including the structural unit derived from the compound, it is possible to obtain a photoresist composition in which rectangularity, resolution, and sensitivity are favorable in the system of a chemically amplified positive resist, and favorable photoresist characteristics are expressed because an acid dissociable, dissolution inhibiting group can be dissociated by an acid generator generating a weak acid.

Moreover, in a photoresist composition of the present invention, etching resistance can be improved. In particular, when a hydrophilic group is introduced into a photoresist composition of the present invention, the adhesion of a resist pattern to a substrate is improved, and the effect of reducing developing defects can be obtained due to the improvement of the affinity of a resist pattern to an alkali developing solution.

A photoresist composition of the present invention is preferably used for patterning of a semiconductor integrated circuit by means of lithography. In particular, an excellent resolution property can be obtained in fine patterning by using a light source with a wavelength of 300 nm or less, for example a KrF, ArF, or $F_2$ excimer laser. Among them, an ArF excimer laser is most preferable. Moreover, a photoresist composition of the present invention is applicable to an electron beam.

A resist pattern formation method of the present invention includes forming a photoresist film on a substrate using the aforementioned photoresist composition; exposing the photoresist film; and developing the exposed photoresist film to form a resist pattern.

A photoresist composition of the present invention forms a resist pattern according to a conventional lithography process. This process is as follows. Firstly, a photoresist composition is coated on a substrate by means of spin-coating or the like, and then dried to form a photoresist film. Next, the photoresist film is selectively exposed through a mask pattern, and then Post Exposure Baking (PEB) is performed. Finally, the exposed photoresist film is developed using an alkaline aqueous solution to form a resist pattern. Herein, a post baking process can be performed according to need.

There is no limitation regarding the light source, although examples of the light source include a far-UV ray with a wavelength of 200 nm or less, specifically an ArF excimer laser, an $F_2$ excimer laser, EUV (extreme ultraviolet light), an electron beam, soft X ray, and X ray. Particularly preferable examples of the light source include a KrF excimer laser, an ArF excimer laser, and an $F_2$ excimer laser. In the case of using a polymer compound (copolymer) using a novel compound of the present invention, an ArF excimer laser is particularly preferable. Moreover, a photoresist composition of the present invention is applicable to an electron beam.

The conditions for a resist pattern formation method including the rotation number of the resist coating, the prebaking temperature, exposure conditions, Post Exposure Baking (PEB) conditions, alkali development conditions can be those conventionally used. In detail, the rotation number is about 1,200 to 3,500 rpm, specifically about 2,000 rpm. The prebaking (PB) temperature is within a range of 70° C. to 130° C. These conditions form a resist film with a thickness of 80 to 300 nm. Exposure can be performed through a mask. A conventional binary mask or a phase-shift mask can be used as a mask for selective exposure. The temperature of Post Exposure Baking (PEB) is within a range of 90° C. to 140° C. As for alkali development conditions, the development is performed using a 1% to 5% by mass of TMAH (tetramethyl ammonium hydroxide) developer at a temperature of 23° C., for 15 to 90 seconds, followed by rinsing with water.

EXAMPLES

Synthesis Example 1

Synthesis of 4-oxo-2-adamantyl chloromethyl ether (The compound represented by the following chemical formula (58). Hereinafter, the compounds in Examples may be referred to as a compound name followed by a formula number such as (58).)

Paraformaldehyde was added to 4-oxo-2-hydroxyadamantane, and a hydrogen chloride gas was injected at 2.5 equivalent amounts per this 4-oxo-2-hydroxyadamantane. Then, the reaction was conducted at a temperature of 50° C. for 12 hours. After the completion of the reaction, the product was distilled under reduced pressure so as to obtain 4-oxo-2-adamantyl chloromethyl ether (compound 1) represented by the following chemical formula (58).

Synthesis Example 2

Synthesis of 2-adamantyl chloromethyl ether (59)

Paraformaldehyde was added to 2-hydroxyadamantane, and a hydrogen chloride gas was injected at 2.5 equivalent amounts per this 2-hydroxyadamantane. Then, the reaction was conducted at a temperature of 50° C. for 12 hours. After the completion of the reaction, the product was distilled under reduced pressure so as to obtain 2-adamantyl chloromethyl ether (compound 2) represented by the following chemical formula (59).

Synthesis Example 3

Synthesis of 1-adamantylmethyl chloromethyl ether (60)

Paraformaldehyde was added to adamantane-1-methanol, and a hydrogen chloride gas was injected at 2.5 equivalent amounts per this adamantane-1-methanol. Then, the reaction was conducted at a temperature of 50° C. for 12 hours. After the completion of the reaction, the product was distilled under reduced pressure so as to obtain 1-adamantylmethyl chloromethyl ether (compound 3) represented by the following chemical formula (60).

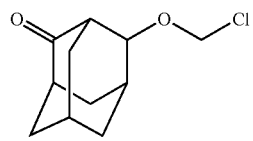

(58)

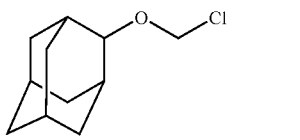

(59)

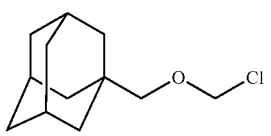

(60)

Synthesis Example 4

Synthesis of 2-adamantyloxymethyl methacrylate (61)

In 200 mL of tetrahydrofuran, 6.9 g of methacrylic acid was dissolved, and then 8.0 g of triethylamine was added. After stirring at room temperature, 100 mL of tetrahydrofuran, in which 15 g of the compound 2 (59) was dissolved, was added dropwise. After stirring at room temperature for 12 hours, the precipitated salt was removed by filtration. The obtained filtrate was evaporated, dissolved in 200 mL of ethyl acetate, washed with pure water (100 mL×3), and then evaporated again. After leaving at freezing point or lower, a white solid substance was obtained. This compound is referred to as the compound 4 and represented by the chemical formula (61). The infrared absorption spectra (IR) and the proton nuclear magnetic resonance spectra ($^1$H-NMR) of the compound 4 were measured, and the results are as follows: IR (cm$^{-1}$): 2907, 2854 (C—H stretch), 1725 (C=O vibration), 1638 (C=C stretch); $^1$H-NMR (CDCl$_3$, internal standard: tetramethylsilane) ppm: 1.45-2.1 (m, 17H), 3.75 (s, 1H), 5.45 (s, 2H), 5.6 (s, 1H), 6.12 (s, 1H)

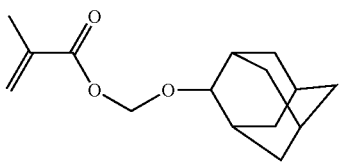

(61)

Synthesis Example 5

Synthesis of 4-oxo-2-adamantyloxymethyl methacrylate (62)

In 50 mL of tetrahydrofuran, 2.2 g of methacrylic acid was dissolved, and then 2.5 g of triethylamine was added. After stirring at room temperature, 50 mL of tetrahydrofuran, in which 4.3 g of the compound 1 (58) was dissolved, was added dropwise. After stirring at room temperature for 12 hours, the precipitated salt was removed by filtration. The obtained filtrate was evaporated, dissolved in 100 mL of ethyl acetate, washed with pure water (50 mL×3), and then evaporated again. After leaving at freezing point or lower, a white solid substance was obtained. This compound is referred to as the compound 5 and represented by chemical formula (62). The infrared absorption spectra (IR) and the proton nuclear magnetic resonance spectra ($^1$H-NMR) of the compound 5 were measured, and the results are as follows: IR (cm$^{-1}$): 2926, 2861 (C—H stretch), 1725 (C=O stretch), 1636 (C=C stretch); $^1$H-NMR (CDCl$_3$, internal standard: tetramethylsilane) ppm: 1.62-3.85 (m, 15H), 4.2 (s, 1H), 5.4 (s, 2H), 5.65 (s, 1H), 6.15 (s, 1H)

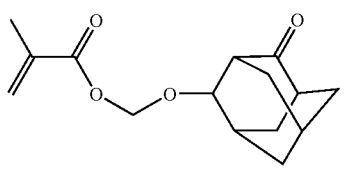

(62)

Synthesis Example 6

Synthesis of 1-adamantylmethyloxymethyl methacrylate (63)

In 200 mL of tetrahydrofuran, 5.5 g of methacrylic acid was dissolved, and then 6.5 g of triethylamine was added. After stirring at room temperature, 100 mL of tetrahydrofuran, in which 12.9 g of the compound 3 (60) was dissolved, was added dropwise. After stirring at room temperature for 12 hours, the precipitated salt was removed by filtration. The obtained filtrate was evaporated, dissolved in 100 mL of ethyl acetate, washed with pure water (100 mL×3), and then evaporated again so as to obtain a colorless oily compound. This compound is referred to as the compound 6 and represented by chemical formula (63). The infrared absorption spectra and the proton nuclear magnetic resonance spectra ($^1$H-NMR) of the compound 6 were measured, and the results are as follows: IR (cm$^{-1}$): 2904, 2850 (C—H stretch), 1727 (C=O stretch), 1638 (C=C vibration); $^1$H-NMR (CDCl$_3$, internal standard: tetramethylsilane) ppm: 1.46-1.96 (m, 18H), 3.22 (s, 2H), 5.34 (s, 2H), 5.6 (s, 1H), 6.15 (s, 1H)

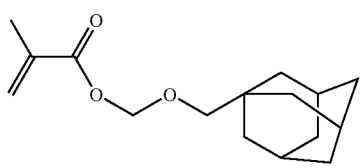

(63)

Synthesis of Resins 1 to 5 Containing the Structural Unit (a1)

Synthesis Example 7

Synthesis of resin 1 (The polymer compound represented by the following chemical formula (64). Hereinafter, the polymer compounds in Examples may be referred to as a resin number followed by a formula number such as (64).)

In 50 mL of tetrahydrofuran, 8.0 g of the compound 4 and 5.4 g of γ-butyrolactone methacrylate were dissolved, and then 0.52 g of azobisisobutylonitrile was added. After refluxing for 24 hours, the reaction solution was added dropwise to 1 L of n-heptane. The precipitated resin was separated by filtration and dried under reduced pressure, and then a white powder resin was obtained. This resin is referred to as the resin 1 and represented by the chemical formula (64). The molecular weight (Mw) of the resin 1 was 21,100. Also, the carbon 13 (hereinafter, carbon 13 means carbon with a mass number of 13) nuclear magnetic resonance spectra ($^{13}$C-NMR) were measured, and the results showed that the composition ratio (hereinafter, the unit of composition ratio is mol %) in the chemical formula was m:n=0.49:0.51.

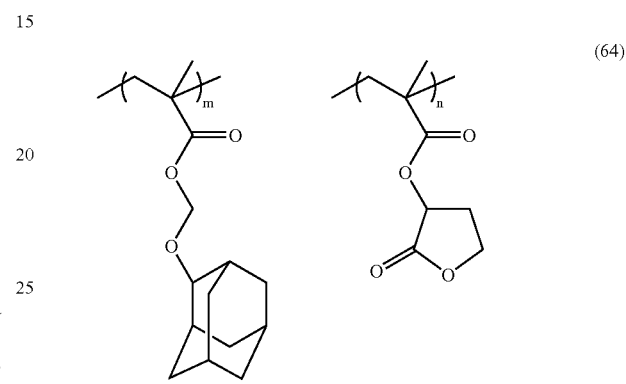

(64)

Synthesis Example 8

Synthesis of Resin 2 (65)

In 20 mL of tetrahydrofuran, 1.0 g of the compound 4, 0.68 g of γ-butyrolactone methacrylate, and 0.47 g of 3-hydroxy-1-adamantyl methacrylate were dissolved, and then 0.08 g of azobisisobutylonitrile was added. After refluxing for 24 hours, the reaction solution was added dropwise to 2 L of n-heptane. The precipitated resin was separated by filtration and dried under reduced pressure, and then a white powder resin was obtained. This resin is referred to as the resin 2 and represented by the chemical formula (65). The molecular weight (Mw) of the resin 2 was 11,500. Also, the carbon 13 nuclear magnetic resonance spectra ($^{13}$C-NMR) were measured, and the results showed that the composition ratio in the chemical formula was m:n:l=0.34:0.42:0.24.

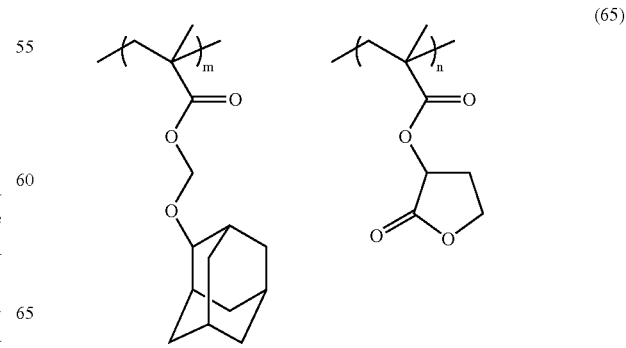

(65)

-continued

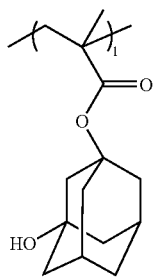

Synthesis Example 9

Synthesis of Resin 3 (66)

In 20 mL of tetrahydrofuran, 1.0 g of the compound 4, 0.68 g of γ-butyrolactone methacrylate, and 0.44 g of 3-hydroxy-1-adamantyl acrylate were dissolved, and then 0.08 g of azobisisobutylonitrile was added. After refluxing for 24 hours, the reaction solution was added dropwise to 2 L of n-heptane. The precipitated resin was separated by filtration and dried under reduced pressure, and then a white powder resin was obtained. This resin is referred to as the resin 3 and represented by the chemical formula (66). The molecular weight (Mw) of the resin 3 was 10,800. Also, the carbon 13 nuclear magnetic resonance spectra ($^{13}$C-NMR) were measured, and the results showed that the composition ratio was m:n:l=0.29:0.45:0.26.

(66)

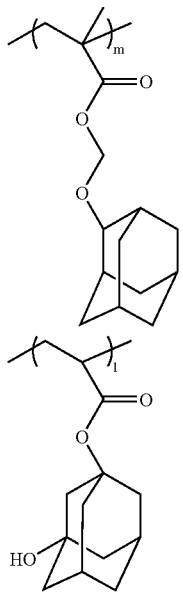

Synthesis Example 10

Synthesis of Resin 4 (67)

In 20 mL of tetrahydrofuran, 1.0 g of the compound 4, 0.68 g of γ-butyrolactone methacrylate, and 0.44 g of norbornane-lactone methacrylate (a monomer corresponding to a structural unit represented by the general formula (49) in which $R^3$ represents a methyl group) were dissolved, and then 0.08 g of azobisisobutylonitrile was added. After refluxing for 24 hours, the reaction solution was added dropwise to 2 L of n-heptane. The precipitated resin was separated by filtration and dried under reduced pressure, and then a white powder resin was obtained. This resin is referred to as the resin 4 and represented by the chemical formula (67). The molecular weight (Mw) of the resin 4 was 12,000. Also, the carbon 13 nuclear magnetic resonance spectra ($^{13}$C-NMR) were measured, and the results showed that the composition ratio was m:n:l=0.37:0.42:0.21.

(67)

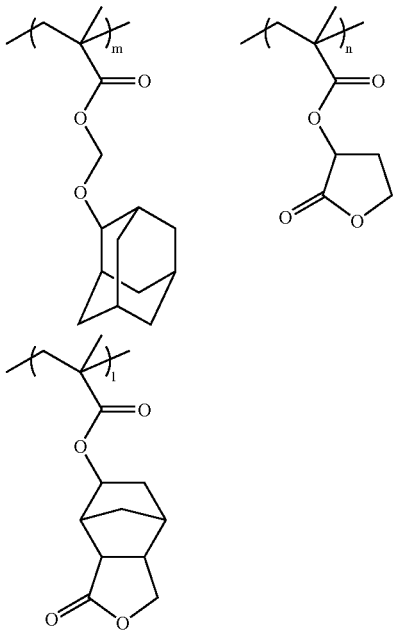

Synthesis Example 11

Synthesis of Resin 5 (68)

In 20 mL of tetrahydrofuran, 1.0 g of the compound 4, 0.68 g of γ-butyrolactone methacrylate, and 0.44 g of norbornane-lactone methacrylate (a monomer corresponding to a structural unit represented by the general formula (48) in which $R^3$ represents a methyl group) were dissolved, and then 0.08 g of azobisisobutylonitrile was added. After refluxing for 24 hours, the reaction solution was added dropwise to 2 L of n-heptane. The precipitated resin was separated by filtration and dried under reduced pressure, and then a white powder resin was obtained. This resin is referred to as the resin 5 and represented by the chemical formula (68). The molecular weight (Mw) of the resin 5 was 12,900. Also, the carbon 13 nuclear magnetic resonance spectra ($^{13}$C-NMR) were measured, and the results showed that the composition ratio was m:n:l=0.36:0.42:0.22.

(68)

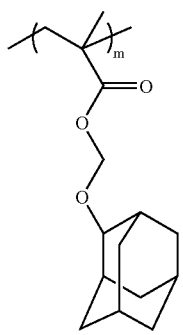

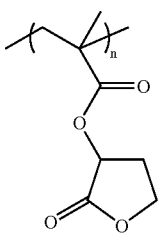

<Synthesis of Resins 7 to 9 in which an Alkli Soluble Group is an Alcoholic Hydroxyl Group>

The following resin 6 synthesized by addition polymerization was used to obtain the resins 7 to 9 in which the compounds 1 to 3 were introduced, respectively. The resins 6 to 9 are represented by the following chemical formulae (69) to (72). The physical properties values of these resins are shown in Table 1.

(69)

(70)

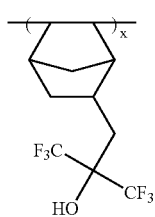

-continued (71)

(72)

(Synthesis of Resin 6 (69))

The resin 6 represented by the chemical formula (69) was synthesized by addition polymerization using a known metal catalyst. In the chemical formula, x represents 100.

Synthesis Example 12

Synthesis of Resin 7 (70)

In 70 mL of tetrahydrofuran, 5.0 g of the resin 6 was dissolved, and then 0.15 g of sodium hydride was added. After stirring until the solution system became homogeneous at room temperature, 0.8 g of the compound 1 was added dropwise. After stirring at room temperature for 12 hours, the precipitated salt was removed by filtration. The obtained filtrate was added dropwise to 1 L of water. The precipitated resin was separated by filtration, dried under reduced pressure, and then dissolved in tetrahydrofuran. This resin solution was added dropwise to 1 L of a mixed solvent of methanol:pure water (80:20). The precipitated resin was separated by filtration and dried under reduced pressure, and then a white powder resin was obtained. This resin is referred to as the resin 7.

Synthesis Example 13

Synthesis of Resin 8 (71)

In 70 mL of tetrahydrofuran, 5.0 g of the resin 6 was dissolved, and then 0.15 g of sodium hydride was added. After stirring until the solution system became homogeneous at room temperature, 0.7 g of the compound 2 was added dropwise. After stirring at room temperature for 12 hours, the precipitated salt was removed by filtration. The obtained filtrate was added dropwise to 1 L of water. The precipitated resin was separated by filtration, dried under reduced pressure, and then dissolved in tetrahydrofuran. This resin solution was added dropwise to 1 L of a mixed solvent of methanol:pure water (80:20). The precipitated resin was separated by filtration and dried under reduced pressure, and then a white powder resin was obtained. This resin is referred to as the resin 8.

Synthesis Example 14

Synthesis of Resin 9 (72)

In 70 mL of tetrahydrofuran, 5.0 g of the resin 6 was dissolved, and then 0.15 g of sodium hydride was added. After stirring until the solution system became homogeneous at room temperature, 0.8 g of the compound 3 was added dropwise. After stirring at room temperature for 12 hours, the precipitated salt was removed by filtration. The obtained filtrate was added dropwise to 1 L of water. The precipitated resin was separated by filtration, dried under reduced pressure, and then dissolved in tetrahydrofuran. This resin solution was added dropwise to 1 L of a mixed solvent of methanol:pure water (80:20). The precipitated resin was separated by filtration and dried under reduced pressure, and then a white powder resin was obtained. This resin is referred to as the resin 9.

TABLE 1

Physical properties values of resins 6 to 9

| | Molecular weight (Mw) | Degree of dispersion (Mw/Mn) | Composition ratio (x/y) |
|---|---|---|---|
| Resin 6 | 8,500 | — | — |
| Resin 7 | 10,900 | 1.49 | 0.78/0.22 |
| Resin 8 | 13,400 | 1.37 | 0.81/0.19 |
| Resin 9 | 10,800 | 1.37 | 0.73/0.27 |

Synthesis of the Resin 10 (74) in which an Alkli Soluble Group is an Phenolic Hydroxyl Group Synthesis Example 15

Synthesis of Resin 10 (74)

In 200 mL of tetrahydrofuran, 24.0 g of a poly-4-hydroxystyrene resin (73) represented by the following chemical formula (73) was dissolved, and then 2.4 g of sodium hydride was added. After stirring until the solution system became homogeneous at room temperature, 12 g of the compound 2 was added dropwise. After stirring at room temperature for 12 hours, the precipitated salt was removed by filtration. The obtained filtrate was added dropwise to 1 L of water. The precipitated resin was separated by filtration, dried under reduced pressure, and then dissolved in tetrahydrofuran. This resin solution was added dropwise to 3 L of n-heptane. The precipitated resin was separated by filtration and dried under reduced pressure, and then a white powder resin was obtained. This resin is referred to as the resin 10. The molecular weight (Mw) and the degree of dispersion (Mw/Mn) of the resin 10 were 12,400 and 1.28, respectively. Also, the proton nuclear magnetic resonance spectra ($^1$H-NMR) were measured, and the results showed that the composition ratio in the chemical formula (74) was m:n=0.87:0.13.

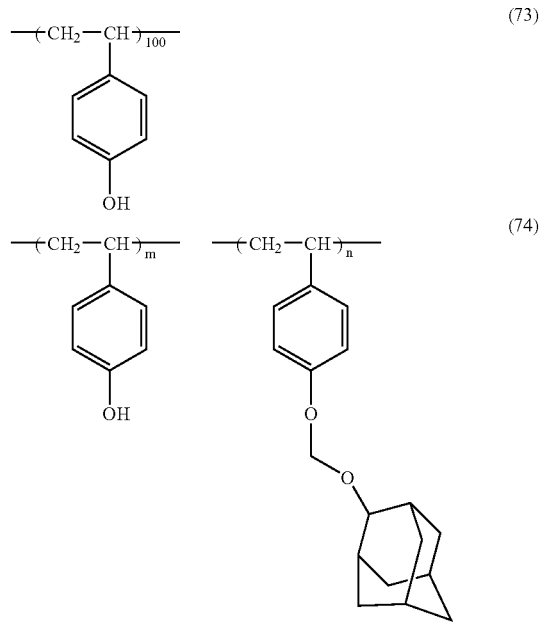

Synthesis of the Resins 11 to 14 Containing the Structural Unit (a1)

Synthesis Example 16

Synthesis of Resin 11 (75)

In 45 mL of tetrahydrofuran, 3.0 g of the compound 4 and 2.0 g of γ-butyrolactone methacrylate were dissolved, and then 0.20 g of azobisisobutylonitrile was added. After refluxing for 12 hours, the reaction solution was added dropwise to 2 L of n-heptane. The precipitated resin was separated by filtration and dried under reduced pressure, and then a white powder resin was obtained. This resin is referred to as the resin 11 and represented by the chemical formula (75). The molecular weight (Mw) and the degree of dispersion (Mw/Mn) of the resin 11 were 12,300 and 1.96, respectively. Also, the carbon 13 nuclear magnetic resonance spectra ($^{13}$C-NMR) were measured, and the results showed that the composition ratio in the chemical formula was m:n=0.47:0.53. Also, the heat decomposition point and the Tg were 257.1° C. and 147.9° C., respectively.

In the present synthesis examples and the comparative synthesis examples, a heat decomposition point was measured by using a thermal analysis apparatus, DSC6200 (manufactured by Seiko Instruments Inc.), under the condition of an increasing temperature of 10° C./min, and Tg (glass transition temperature) was measured by using a thermal analysis apparatus, TG/DTA6200 (manufactured by Seiko Instruments Inc.), under the condition of an increasing temperature of 10° C./min.

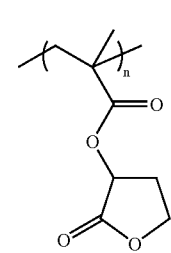

(75)

Synthesis Example 17

Synthesis of Resin 12 (77)

In 60 mL of tetrahydrofuran, 3.0 g of the compound 4 and 4.0 g of the compound 7 represented by the following chemical formula (76) were dissolved, and then 0.20 g of azobisisobutylonitrile was added. After refluxing for 12 hours, the reaction solution was added dropwise to 2 L of n-heptane. The precipitated resin was separated by filtration and dried under reduced pressure, and then a white powder resin was obtained. This resin is referred to as the resin 12 and represented by the chemical formula (77). The molecular weight (Mw) and the degree of dispersion (Mw/Mn) of the resin 12 were 9,800 and 1.61, respectively. Also, the carbon 13 nuclear magnetic resonance spectra ($^{13}$C-NMR) were measured, and the results showed that the composition ratio in the chemical formula was m:n=0.57:0.43. Also, the heat decomposition point and the Tg were 234.5° C. and 114.1° C., respectively.

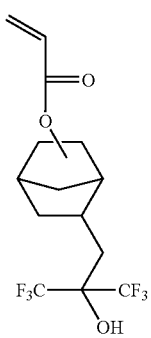

(76)

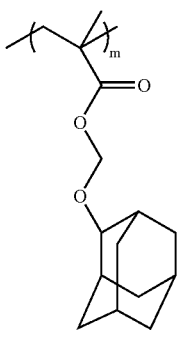

(77)

Synthesis Example 18

Synthesis of Resin 13 (78)

In 90 mL of tetrahydrofuran, 6.0 g of the compound 6 and 3.9 g of γ-butyrolactone methacrylate were dissolved, and then 0.37 g of azobisisobutylonitrile was added. After refluxing for 12 hours, the reaction solution was added dropwise to 2 L of n-heptane. The precipitated resin was separated by filtration and dried under reduced pressure, and then a white powder resin was obtained. This resin is referred to as the resin 13 and represented by the chemical formula (78). The molecular weight (Mw) and the degree of dispersion (Mw/Mn) of the resin 13 were 12,800 and 1.87, respectively. Also, the carbon 13 nuclear magnetic resonance spectra ($^{13}$C-NMR) were measured, and the results showed that the composition ratio in the chemical formula was m:n=0.43:0.57. Also, the heat decomposition point and the Tg were 240.0° C. and 142.2° C., respectively.

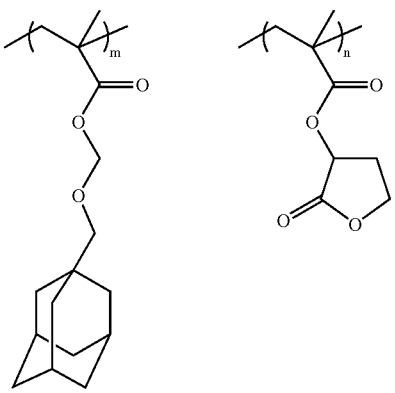

(78)

Synthesis Example 19

Synthesis of Resin 14 (79)

In 120 mL of tetrahydrofuran, 6.0 g of the compound 6 and 7.6 g of the compound 7 were dissolved, and then 0.37 g of azobisisobutylonitrile was added. After refluxing for 12 hours, the reaction solution was added dropwise to 2 L of n-heptane. The precipitated resin was separated by filtration and dried under reduced pressure, and then a white powder resin was obtained. This resin is referred to as the resin 14 and represented by the chemical formula (79). The molecular weight (Mw) and the degree of dispersion (Mw/Mn) of the resin 14 were 11,600 and 1.60, respectively. Also, the carbon 13 nuclear magnetic resonance spectra ($^{13}$C-NMR) were measured, and the results showed that the composition ratio in the chemical formula was m:n=0.56:0.44. Also, the heat decomposition point and the Tg were 233.6° C. and 109.4° C., respectively.

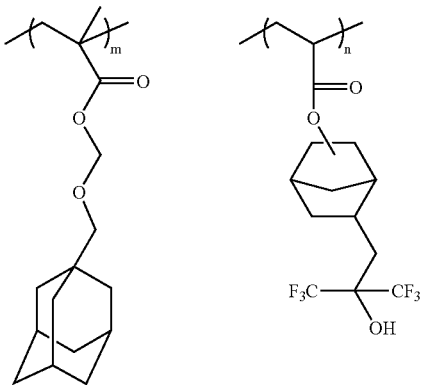

(79)

Synthesis of Comparative Resins 1 to 4 as Comparative Examples

Comparative Synthesis Example 1

Synthesis of Comparative Resin 1 (80)

In 140 mL of tetrahydrofuran, 9.9 g of 2-methyl-2-adamantyl methacrylate and 6.0 g of γ-butyrolactone methacrylate were dissolved, and then 0.63 g of azobisisobutylonitrile was added. After refluxing for 12 hours, the reaction solution was added dropwise to 2 L of n-heptane. The precipitated resin was separated by filtration and dried under reduced pressure, and then a white powder resin was obtained. This resin is referred to as the comparative resin 1 and represented by the chemical formula (80). The molecular weight (Mw) and the degree of dispersion (Mw/Mn) of the comparative resin 1 were 8,700 and 1.83, respectively. Also, the carbon 13 nuclear magnetic resonance spectra ($^{13}$C-NMR) were measured, and the results showed that the composition ratio in the chemical formula was m:n=0.41:0.59. Also, the heat decomposition point and the Tg were 222.5° C. and 158.9° C., respectively.

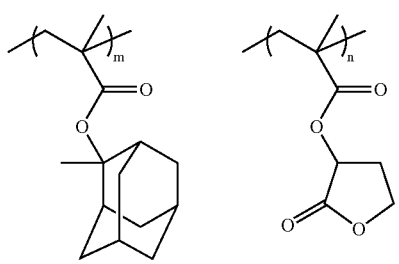

(80)

Comparative Synthesis Example 2

Synthesis of Comparative Resin 2 (81)

In 230 mL of tetrahydrofuran, 10.6 g of 2-methyl-2-adamantyl methacrylate and 15.0 g of the compound 7 were dissolved, and then 0.74 g of azobisisobutylonitrile was added. After refluxing for 12 hours, the reaction solution was added dropwise to 2 L of n-heptane. The precipitated resin was separated by filtration and dried under reduced pressure, and then a white powder resin was obtained. This resin is referred to as the comparative resin 2 and represented by the chemical formula (81). The molecular weight (Mw) and the degree of dispersion (Mw/Mn) of the comparative resin 2 were 8,780 and 1.42, respectively. Also, the carbon 13 nuclear magnetic resonance spectra ($^{13}$C-NMR) were measured, and the results showed that the composition ratio in the chemical formula was m:n=0.64:0.36. Also, the heat decomposition point and the Tg were 215.7° C. and 133.3° C., respectively.

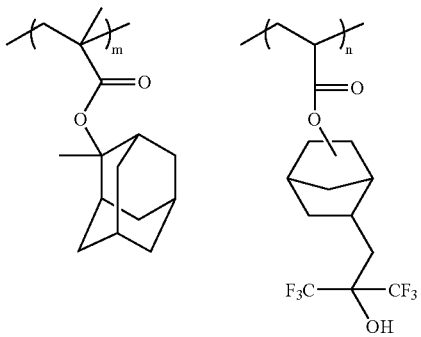

(81)

Comparative Synthesis Example 3

Synthesis of Comparative Resin 3 (83)

In 100 mL of tetrahydrofuran, 15 g of the comparative resin 3' (manufactured by Promerus LLC; weight average molecular weight=7,640, degree of dispersion=1.93) represented by the following chemical formula (82) was dissolved, and then 0.88 g of sodium hydride was added. After stirring until the solution system became homogeneous at room temperature, 1.76 g of chloromethyl methyl ether (manufactured by Tokyo Ohka Kogyo Co., Ltd.) was added dropwise. After stirring at room temperature for 12 hours, the precipitated salt was removed by filtration. The obtained filtrate was added dropwise to 1 L of water. The precipitated resin was separated by filtration, dried under reduced pressure, and then dissolved in tetrahydrofuran. This resin solution was added dropwise to 1 L of n-heptane. The precipitated resin was separated by filtration and dried under reduced pressure, and then a white powder resin was obtained. The yield was 5.0 g. This resin is referred to as the comparative resin 3 and represented by the chemical formula (83). The weight average molecular weight (Mw) and the degree of dispersion (Mw/Mn) of the comparative resin 3 were 14,000 and 2.14, respectively. The protection rate of a hydroxyl group was 40.7%.

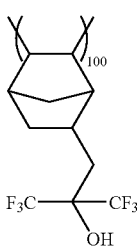

(82)

-continued

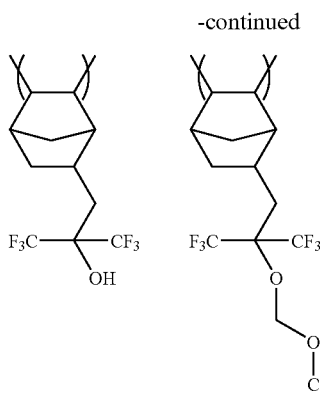
(83)

Comparative Synthesis Example 4

Synthesis of Comparative Resin 4 (83)

The protection rate was changed in Comparative synthesis example 3. In other words, the reaction was conducted by using the same process other than adjusting the amount of chloromethyl methyl ether. The weight average molecular weight (Mw) and the degree of dispersion (Mw/Mn) of the obtained resin were 13,900 and 2.23, respectively. The protection rate of a hydroxyl group was 20.8%. This resin is referred to as the comparative resin 4 and represented by the chemical formula (83).

Examples 1 to 3

Confirmation of the Exposure Resolution of a Positive Photoresist

The resolution of a positive photoresist was confirmed by using the resins 7 to 9. An ArF excimer laser was used for exposure. The positive photoresist composition was prepared by mixing each of the resins 7 to 9 with the acid generator, the nitrogen-containing organic compound, and the solvent, each being described below.

| | |
|---|---|
| Resins 7 to 9 | 100 parts by mass |
| Acid generator: TPS-PFBS | 2.0 parts by mass |
| Nitrogen-containing organic compound: triisopropanolamine | 0.2 parts by mass |
| Organic solvent: PGMEA | 1250 parts by mass |

"TPS-PFBS" represents triphenylsulfonium perfluorobutanesulfonate, and "PGMEA" represents propylene glycol monomethyl ether acetate.

"TPS-PFBS" represents triphenylsulfonium perfluorobutanesulfonate, and "PGMEA" represents propylene glycol monomethyl ether acetate.

The exposure resolution of the positive photoresist was confirmed under the conditions shown in following Table 2.

TABLE 2

Conditions for evaluating exposure resolution of positive photoresist

| | |
|---|---|
| Substrate | Organic anti-reflective film: AR-19 (manufactured by Shipley Ltd.) |
| Thickness of resist film | 300 nm |

TABLE 2-continued

Conditions for evaluating exposure resolution of positive photoresist

| | |
|---|---|
| Exposure apparatus | Nikon NSR-S302 (NA 0.60, 2/3 annular) |
| Baking condition | PB: 110° C., 90 seconds |
| | PEB: 90° C., 60 seconds |
| Developing condition | NMD-3 2.38% (manufactured by Tokyo Ohka Kogyo Co. Ltd.), 30 seconds |

"Developing condition: NMD-3 2.38% (manufactured by Tokyo Ohka Kogyo Co. Ltd.), 30 seconds" means that the development was performed by using NMD-3 2.38% (trade name, manufactured by Tokyo Ohka Kogyo Co. Ltd.) under the condition of a developing time of 30 seconds.

"Developing condition: NMD-3 2.38% (manufactured by Tokyo Ohka Kogyo Co. Ltd.), 30 seconds" means that the development was performed by using NMD-3 2.38% (trade name, manufactured by Tokyo Ohka Kogyo Co. Ltd.) under the condition of a developing time of 30 seconds.

The evaluation of the exposure resolution is shown in the following Table 3. By using the positive photoresist compositions (Examples 1 to 3) including each of the resins 7 to 9 which is the specific examples of a polymer compound of the present invention, it was found that a line and space pattern of 120 nm was obtained on 1:1 and that the pattern shape showed rectangularity. The exposure in this time was 14 to 15 mJ/cm$^2$, and the favorable sensitivity was obtained.

TABLE 3

Evaluation of resolution and exposure

| | Resolution (line and space) | Sensitivity (mJ/cm$^2$) |
|---|---|---|
| Resin 7 | 120 nm | 15 |
| Resin 8 | 120 nm | 15 |
| Resin 9 | 120 nm | 14 |

Example 4

The performance of a positive photoresist was confirmed by using the resin 1 from a thickness change of a resist film when an exposure is changed. The positive photoresist composition was prepared by mixing the resin 1 with the acid generator, the nitrogen-containing organic compound, and the solvent, each being described below.

| | |
|---|---|
| Resin 1 | 100 parts by mass |
| Acid generator: TPS-PFBS | 2.0 parts by mass |
| Nitrogen-containing organic compound: triisopropanolamine | 0.2 parts by mass |
| Organic solvent: PGMEA | 1250 parts by mass |

As can be seen from the sensitivity profile obtained by using ArF exposure, the performance of the positive photoresist was able to be confirmed. Also, the sensitivity was favorable.

Examples 5 to 8

The resolution of a positive photoresist was confirmed by using the resins 2 to 5. An ArF excimer laser was used for exposure. The positive photoresist composition was prepared by mixing each of the resins 2 to 5 with the acid generator, the nitrogen-containing organic compound, and the solvent, each being described below.

| | |
|---|---|
| Resins 2 to 5 | 100 parts by mass |
| Acid generator: TPS-PFBS | 3.0 parts by mass |
| Nitrogen-containing organic compound: triisopropanolamine | 0.35 parts by mass |
| Organic solvent:   PGMEA | 1250 parts by mass |
|                             GBL | 125 parts by mass |

"GBL" represents γ-butyrolactone.

"GBL" represents γ-butyrolactone.

The exposure resolution of the positive photoresist was confirmed under the conditions shown in following Table 4.

TABLE 4

| | |
|---|---|
| Substrate | Organic anti-reflective film: ARC29 (manufactured by Brewer Science Ltd.) |
| Thickness of resist film | 300 nm |
| Exposure apparatus | Nikon NSR-S302 (NA 0.60, 2/3 annular) |
| Baking condition | PB: 110° C., 90 seconds<br>PEB: 110° C., 90 seconds |
| Developing condition | NMD-3 2.38% (manufactured by Tokyo Ohka Kogyo Co. Ltd.), 60 seconds |

The evaluation of the exposure resolution is shown in the following Table 5. By using the positive photoresist compositions (Examples 5 to 8) including the resins 2 to 5, respectively, which are the specific examples of a polymer compound of the present invention, it was found that a line and space pattern of 120 nm was obtained on 1:1 and that the pattern shape showed rectangularity. The exposure (sensitivity) in this time was shown in Table 5.

TABLE 5

| | Resolution and exposure | |
|---|---|---|
| | Resolution (line and space) | Sensitivity (mJ/cm$^2$) |
| Resin 2 | 120 nm | 37 |
| Resin 3 | 120 nm | 33 |
| Resin 4 | 120 nm | 37 |
| Resin 5 | 120 nm | 41 |

Examples 9 to 19 and Comparative Examples 1 to 8

The positive resist compositions, which have the compositions shown in following Table 6, were prepared, and then resist patterns were formed under the conditions shown in Table 7 and evaluated. The results are shown in Table 8.

TABLE 6

| | (A) Resin | (B) Acid generator | (D) Nitrogen-containing organic compound | Organic solvent |
|---|---|---|---|---|
| Example 9 | Resin 11 (100 parts by mass) | PAG1 (3 parts by mass) | Triethanolamine (0.3 parts by weight) | PGMEA (750 parts by weight) EL (500 parts by weight) |
| Example 10 | Resin 11 (100 parts by mass) | PAG2 (3.4 parts by mass) | Triethanolamine (0.3 parts by weight) | PGMEA (750 parts by weight) EL (500 parts by weight) |
| Example 11 | Resin 11 (100 parts by mass) | PAG3 (5 parts by mass) | Triethanolamine (0.3 parts by weight) | PGMEA (750 parts by weight) EL (500 parts by weight) |
| Example 12 | Resin 12 (100 parts by mass) | PAG1 (3 parts by mass) | Triethanolamine (0.3 parts by weight) | PGMEA (750 parts by weight) EL (500 parts by weight) |
| Example 13 | Resin 12 (100 parts by mass) | PAG2 (3.4 parts by mass) | Triethanolamine (0.3 parts by weight) | PGMEA (750 parts by weight) EL (500 parts by weight) |
| Example 14 | Resin 12 (100 parts by mass) | PAG3 (5 parts by mass) | Triethanolamine (0.3 parts by weight) | PGMEA (750 parts by weight) EL (500 parts by weight) |
| Example 15 | Resin 13 (100 parts by mass) | PAG1 (3 parts by mass) | Triethanolamine (0.3 parts by weight) | PGMEA (750 parts by weight) EL (500 parts by weight) |
| Example 16 | Resin 13 (100 parts by mass) | PAG3 (5 parts by mass) | Triethanolamine (0.3 parts by weight) | PGMEA (750 parts by weight) EL (500 parts by weight) |
| Example 17 | Resin 14 (100 parts by mass) | PAG1 (3 parts by mass) | Triethanolamine (0.3 parts by weight) | PGMEA (750 parts by weight) EL (500 parts by weight) |
| Example 18 | Resin 14 (100 parts by mass) | PAG2 (3.4 parts by mass) | Triethanolamine (0.3 parts by weight) | PGMEA (750 parts by weight) EL (500 parts by weight) |
| Example 19 | Resin 14 (100 parts by mass) | PAG3 (5 parts by mass) | Triethanolamine (0.3 parts by weight) | PGMEA (750 parts by weight) EL (500 parts by weight) |
| Comparative example 1 | Comparative resin 1 (100 parts by mass) | PAG1 (3 parts by mass) | Triethanolamine (0.3 parts by weight) | PGMEA (750 parts by weight) EL (500 parts by weight) |
| Comparative example 2 | Comparative resin 1 (100 parts by mass) | PAG2 (3.4 parts by mass) | Triethanolamine (0.3 parts by weight) | PGMEA (750 parts by weight) EL (500 parts by weight) |
| Comparative example 3 | Comparative resin 1 (100 parts by mass) | PAG3 (5 parts by mass) | Triethanolamine (0.3 parts by weight) | PGMEA (750 parts by weight) EL (500 parts by weight) |
| Comparative example 4 | Comparative resin 2 (100 parts by mass) | PAG1 (3 parts by mass) | Triethanolamine (0.3 parts by weight) | PGMEA (750 parts by weight) EL (500 parts by weight) |
| Comparative example 5 | Comparative resin 2 (100 parts by mass) | PAG2 (3.4 parts by mass) | Triethanolamine (0.3 parts by weight) | PGMEA (750 parts by weight) EL (500 parts by weight) |
| Comparative example 6 | Comparative resin 2 (100 parts by mass) | PAG3 (5 parts by mass) | Triethanolamine (0.3 parts by weight) | PGMEA (750 parts by weight) EL (500 parts by weight) |
| Comparative example 7 | Comparative resin 3 (100 parts by mass) | PAG1 (2 parts by mass) | Triisopropanolamine (0.1 parts by weight) | PGMEA (1150 parts by weight) |
| Comparative example 8 | Comparative resin 4 (100 parts by mass) | PAG1 (2 parts by mass) | Triisopropanolamine (0.1 parts by weight) | PGMEA (1150 parts by weight) |

The abbreviations in Table 6 represent the following.

PAG1: triphenylsulfonium nonafluorobutanesulfonate

PAG2: bis(2,4-dimethylphenylsulfonyl)diazomethane represented by the following chemical formula (84)

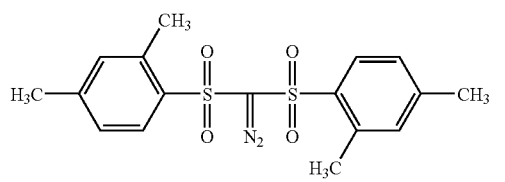

(84)

PAG3: camphor sulfonic acid of triphenylsulfonium represented by the following chemical formula (85)

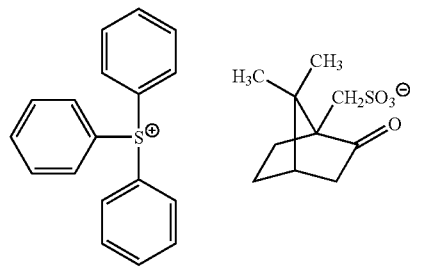

(85)

PGMEA: propylene glycol monomethyl ether acetate

EL: ethyl lactate

TABLE 7

| Substrate: | organic anti-reflective film AR-29 (manufactured by Shipley Ltd.) |
|---|---|
| Thickness of resist film: | 250 nm |
| Exposure apparatus: | Nikon NSR-S302 (NA = 0.6, 2/3 annular) |
| Baking condition: | PB 100° C./90 seconds PEB 100° C./90 seconds |
| Developing condition: | NMD-3 2.38% (manufactured by Tokyo Ohka Kogyo Co. Ltd.), 23° C./60 seconds |

The conditions for Comparative examples 7 and 8 were the same as the conditions shown in Table 2 other than changing the thickness of a resist film to 200 nm.

TABLE 8

| | Resolution (nm) line and space | Sensitivity (mJ/cm$^2$) |
|---|---|---|
| Example 9 | 110 | 19 |
| Example 10 | 150 | 54 |
| Example 11 | 110 | 19 |

TABLE 8-continued

| | Resolution (nm) line and space | Sensitivity (mJ/cm$^2$) |
|---|---|---|
| Example 12 | 110 | 17 |
| Example 13 | 110 | 21 |
| Example 14 | 130 | 10 |
| Example 15 | 110 | 19 |
| Example 16 | 110 | 23 |
| Example 17 | 110 | 18 |
| Example 18 | 120 | 28 |
| Example 19 | 150 | 12 |
| Comparative example 1 | 110 | 38 |
| Comparative example 2 | not resolved | — |
| Comparative example 3 | not resolved | — |
| Comparative example 4 | 110 | 26 |
| Comparative example 5 | not resolved | — |
| Comparative example 6 | 170 | 36 |
| Comparative example 7 | not resolved | — |
| Comparative example 8 | Thickness of the resist pattern was lost, and the pattern disappeared. | — |

When PAG2 was used, any resist pattern was not resolved in Comparative examples 2 and 5. In contrast, the resist patterns of line and space were obtained in Examples 10, 13, and 18.

When PAG3 was used, any resist pattern was not resolved in Comparative example 3, and the resist pattern of line and space of 170 nm was obtained in Comparative example 6. In comparison to these Comparative examples, resolution and sensitivity were improved in Examples 11, 14, and 19.

Line and space patterns with a line width of 120 nm and a pitch of 240 nm were formed, and in Examples 9, 12, and 15 and Comparative examples 1 and 4, 3σ was measured, which is a measure of indicating LER (line edge roughness: unevenness of line side wall). In the present Example, 3σ was measured by the length-measuring SEM (manufactured by Hitachi Ltd., trade name: "S-9220"). The lower 3σ means that a resist pattern with the smaller roughness and even width is obtained. The results showed that 3 σ was 6.4 nm in Example 9, 5.4 nm in Example 12, 6.9 nm in Example 15, 9.0 nm in Comparative example 1, and 6.9 nm in Comparative example 4. From these results, it was found that LER was reduced by using a structural unit (a1) of the present invention.

When PAG1 was used, resolution was about the same, whereas sensitivity was improved in Examples 9, 12, 15, and 17.

Examples 20 to 21 and Comparative Example 9

The resist compositions, which have the compositions shown in following Table 9, were prepared, and then resist patterns were formed under the packaging conditions shown in Table 10 and evaluated. The results are shown in Table 11.

TABLE 9

| | (A) Resin | (B) Acid generator | (D) Nitrogen-containing organic compound | Organic solvent |
|---|---|---|---|---|
| Example 20 | Resin 11 (100 parts by mass) | PAG1 (3 parts by mass) | Triethanolamine (0.3 parts by weight) | PGMEA (1250 parts by weight) |
| Example 21 | Resin 12 (100 parts by mass) | PAG1 (3 parts by mass) | Triethanolamine (0.3 parts by weight) | PGMEA (1250 parts by weight) |
| Comparative example 9 | Comparative resin 1 (100 parts by mass) | PAG1 (5 parts by mass) | Triethanolamine (0.3 parts by weight) | PGMEA (1250 parts by weight) |

PAG1: triphenylsulfonium nonafluorobutanesulfonate

TABLE 10

| Substrate: | 8-inch diameter silicon wafer |
|---|---|
| Thickness of resist film: | 200 nm |
| Exposure apparatus: | Hitachi Ltd. HL-800D (Accelerating voltage 70 kV) |
| Baking condition: | PB 120° C./90 seconds |
| | PEB 120° C./60 seconds |
| Developing condition: | NMD-3 2.38% (manufactured by Tokyo Ohka Kogyo Co. Ltd.), 23° C./60 seconds |

TABLE 11

| | Resolution (nm) line and space | Sensitivity ($\mu C/cm^2$) | LER (nm) |
|---|---|---|---|
| Example 20 | 90 | 70 | 7.2 |
| Example 21 | 90 | 59 | 8.2 |
| Comparative example 9 | 160 | 114 | 8 |

In Table 11, sensitivity and LER are as follows.

Sensitivity: In Examples 20 to 21, sensitivity was measured when the size of a line and space pattern of 100 nm became 1:1. In Comparative example 9, sensitivity was measured when the size of a line and space pattern of 160 nm became 1:1.

LER: In Examples 20 to 21, LER was measured when the size of a line and space pattern of 100 nm became 1:1. In Comparative example 9, LER was measured when the size of a line and space pattern of 160 nm became 1:1.

From the aforementioned results, it was found that a resist composition of the present invention was excellent in resolution, sensitivity, and LER even when electron beam was used as a light source for exposure.

Synthesis Examples 20 to 25

In the similar process of Synthesis example 8, the resins 15 to 20 were synthesized, which have the common structural formula described below and the different composition ratios. The results are shown in Table 12.

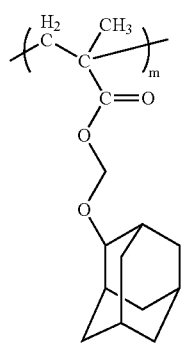
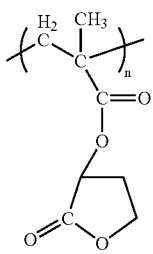

-continued

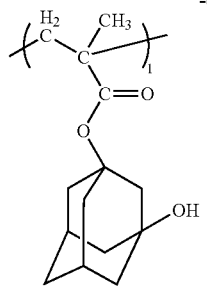

Synthesis Example 26

In 640 mL of tetrahydrofuran, 38.8 g of (4-oxo-2-adamantyloxy)methyl methacrylate (corresponding to the compound 5 in Synthesis example 5) and 25.0 g of γ-butyrolactone methacrylate were dissolved, and then 2.41 g of azobisisobutylonitrile was added. After refluxing for 6 hours, the reaction solution was added dropwise to 2 L of methanol. The precipitated resin was separated by filtration and dried under reduced pressure, and then a white powder resin was obtained. This resin is referred to as the resin 21 and represented by the structural formula described below. The molecular weight (Mw) and the degree of dispersion (Mw/Mn) of the resin 21 were 12,400 and 2.01, respectively. Also, the carbon 13 nuclear magnetic resonance spectra ($^{13}C$-NMR) were measured, and the results showed that the composition ratio was m:n=0.48:0.52. The results are shown in Table 12.

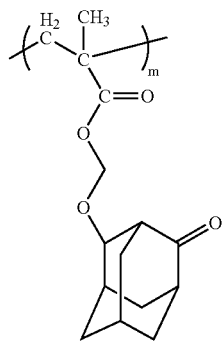
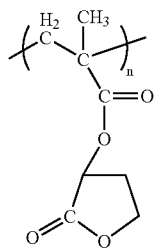

Comparative Synthesis Example 5

In 200 mL of tetrahydrofuran, 18.7 g of 2-methyl-2-adamantyl methacrylate, 13.6 g of γ-butyrolactone methacrylate, and 9.5 g of 3-hydroxy-1-adamantyl methacrylate were dissolved, and then 1.64 g of azobisisobutylonitrile was added. After refluxing for 6 hours, the reaction solution was added dropwise to 1 L of n-heptane. The precipitated resin was separated by filtration and dried under reduced pressure, and then a white powder resin was obtained. This resin is referred to as the comparative resin 5 and represented by the structural formula described below. The weight average molecular weight (Mw) and the degree of dispersion (Mw/Mn) of the comparative resin 5 were 10,000 and 2.0, respectively. Also, the carbon 13 nuclear magnetic resonance spectra ($^{13}$C-NMR) were measured, and the results showed that the composition ratio of the structural units represented by the structural formula described below was m:n:l=0.4:0.4:0.2.

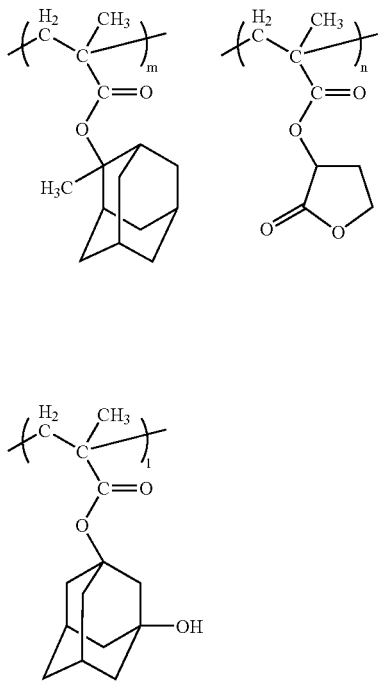

Comparative Synthesis Example 6

In the similar process of Comparative synthesis example 1, the comparative resin 6 was synthesized. The weight average molecular weight (Mw) and the degree of dispersion (Mw/Mn) of the comparative resin 6 were 9,200 and 1.96, respectively. Also, the carbon 13 nuclear magnetic resonance spectra ($^{13}$C-NMR) were measured, and the results showed that the composition ratio of the structural units represented by the structural formula described below was m:n=0.44:0.56.

TABLE 12

|  | Composition ratio (m/n/l) | Molecular weight (Mw) | Degree of dispersion (Mw/Mn) |
|---|---|---|---|
| Resin 15 | 0.4/0.4/0.2 | 9,700 | 1.88 |
| Resin 16 | 0.4/0.4/0.2 | 6,000 | 1.69 |
| Resin 17 | 0.4/0.4/0.2 | 14,400 | 1.93 |
| Resin 18 | 0.3/0.4/0.3 | 11,100 | 1.91 |
| Resin 19 | 0.3/0.5/0.2 | 9,600 | 1.77 |
| Resin 20 | 0.2/0.6/0.2 | 9,600 | 1.62 |
| Resin 21 | 0.48/0.52/0 | 11,700 | 2.01 |
| Comparative resin 5 | 0.4/0.4/0.2 | 10,000 | 2.0 |
| Comparative resin 6 | 0.44/0.56/0 | 9,200 | 1.96 |

Examples 22 to 27 and Comparative Example 10

The positive resist compositions, which have the compositions represented by following Table 13, were prepared.

Subsequently, an organic anti-reflective film material (manufactured by Brewer Science Ltd., trade name "ARC-29") was coated on top of an 8-inch diameter silicon wafer and baked at 225° C. for 60 seconds, thereby forming an anti-reflective film as a substrate.

On the substrate, the aforementioned positive photoresist composition was uniformly coated by using a spinner and then dried by prebaking (PAB) under the conditions shown in Table 14, thereby forming a resist layer. Subsequently, the resist layer was selectively exposed by using the ArF exposure apparatus (wavelength: 193 nm) NSR-S302 (manufactured by Nikon Corporation, NA (numerical aperture)=0.60, ⅔ annular) through a mask.

Then, the exposed photoresist was subjected to a PEB treatment under the conditions shown in Table 14 followed by puddle development for 30 seconds at 23° C. in a 2.38% by mass aqueous solution of tetramethylammonium hydroxide, rinsed with pure water for 30 seconds, and then dried by shaking so as to form a resist pattern of line and space (1:1) of 140 nm (hereinafter referred to as a L/S pattern).

TABLE 13

|  | (A) Resin (parts by mass) | (B) Acid generator (parts by mass) | (D) Nitrogen-containing organic compound (parts by mass) | Organic solvent (parts by mass) | Surfactant (parts by mass) |
|---|---|---|---|---|---|
| Example 22 | Resin 15 (100) | PAG1 (3) | Triethanolamine (0.35) | PGMEA (1230) | — |
| Example 23 | Resin 16 (100) | PAG1 (3) | Triethanolamine (0.35) | PGMEA (1230) | — |
| Example 24 | Resin 17 (100) | PAG1 (3) | Triethanolamine (0.35) | PGMEA (1230) | — |
| Example 25 | Resin 18 (100) | PAG1 (3) | Triethanolamine (0.35) | PGMEA (1230) | — |
| Example 26 | Resin 19 (100) | PAG1 (3) | Triethanolamine (0.35) | PGMEA (1230) | — |

TABLE 13-continued

| | (A) Resin (parts by mass) | (B) Acid generator (parts by mass) | (D) Nitrogen-containing organic compound (parts by mass) | Organic solvent (parts by mass) | Surfactant (parts by mass) |
|---|---|---|---|---|---|
| Example 27 | Resin 20 (100) | PAG1 (3) | Triethanolamine (0.35) | PGMEA (1230) | — |
| Example 28 | Resin 21 (100) | PAG1 (3) | Triethanolamine (0.3) | PGMEA (750) EL (500) | — |
| Comparative example 10 | Comparative resin 5 (100) | PAG1 (3) | Triethanolamine (0.25) | PGMEA (1250) | — |
| Comparative example 11 | Comparative resin 6 (100) | PAG2 (2) PAG3 (0.8) | Triethanolamine (0.25) | PGMEA (1250) PGME (500) GBL (25) | XR-104 (0.1) |

PAG1: triphenylsulfonium nonafluorobutanesulfonate
PAG2: 4-methylphenyldiphenylsulfonium nonafluorobutanesulfonate
PAG3: tri(4-tert-butylphenyl)sulfonium trifluoromethanesulfonate
XR-104 (trade name): produced by Dainippon Ink and Chemicals, Incorporated
PGME: propylene glycol monomethyl ether

TABLE 14

| | Anti-reflective film upper: material lower: film thickness | Thickness of resist film | Prebaking (PAB) conditions | PEB conditions |
|---|---|---|---|---|
| Example 22 | ARC-29 38 nm | 225 nm | 95° C./90 seconds | 105° C./90 seconds |
| Example 23 | ARC-29 38 nm | 225 nm | 95° C./90 seconds | 105° C./90 seconds |
| Example 24 | ARC-29 38 nm | 225 nm | 95° C./90 seconds | 105° C./90 seconds |
| Example 25 | ARC-29 38 nm | 225 nm | 95° C./90 seconds | 105° C./90 seconds |
| Example 26 | ARC-29 38 nm | 225 nm | 95° C./90 seconds | 105° C./90 seconds |
| Example 27 | ARC-29 38 nm | 225 nm | 95° C./90 seconds | 105° C./90 seconds |
| Example 28 | ARC-29 77 nm | 250 nm | 120° C./90 seconds | 120° C./90 seconds |
| Comparative example 10 | ARC-29 38 nm | 225 nm | 125° C./90 seconds | 135° C./90 seconds |
| Comparative example 11 | ARC-29 77 nm | 250 nm | 120° C./90 seconds | 120° C./90 seconds |

The following evaluation was performed, and the results are shown in Table 15.

(Exposure Margin)

Exposure margin, which is obtained by exposure (sensitivity) (Eop) to exactly resolve a L/S pattern of 140 nm on 1:1 and fluctuation range of exposure (fluctuation range of sensitivity) to resolve a L/S pattern of 140 nm±10%, was calculated by using the following formula.

Exposure margin={$E$(126nm)−$E$(154nm)}×100/$Eop$

Eop: sensitivity to obtain a L/S pattern of 140 nm on exactly 1:1 (mJ/cm$^2$)

E (154 nm): sensitivity to obtain an L/S pattern of 150 nm (mJ/cm$^2$)

E (126 nm): sensitivity to obtain an L/S pattern of 126 nm (mJ/cm$^2$)

TABLE 15

| | Exposure margin (%) |
|---|---|
| Example 22 | 16.0 |
| Example 23 | 15.9 |
| Example 24 | 16.8 |
| Example 25 | 13.1 |
| Example 26 | 15.5 |
| Example 27 | 13.4 |
| Comparative example 10 | 12.7 |

Example 28 and Comparative Example 11

The positive resist compositions, which have the compositions shown in following Table 13, were prepared.

Subsequently, an organic anti-reflective film material (manufactured by Brewer Science Ltd., trade name "ARC-29") was coated on top of an 8-inch diameter silicon wafer and baked at 225° C. for 60 seconds, thereby forming an anti-reflective film as a substrate.

On the substrate, the obtained positive photoresist composition was uniformly coated by using a spinner and then dried by prebaking under the conditions shown in Table 14, thereby forming a resist layer. Subsequently, the resist layer was selectively exposed by using the ArF exposure apparatus (wavelength: 193 nm) NSR-S302 (manufactured by Nikon Corporation, NA (numerical aperture)=0.60, ⅔ annular) through a mask.

Then, the exposed photoresist was subjected to a PEB treatment under the conditions shown in Table 14 followed by puddle development for 30 seconds at 23° C. in a 2.38% by mass aqueous solution of tetramethylammonium hydroxide, rinsed with pure water for 30 seconds, and then dried by shaking so as to form a resist pattern of line and space (1:1) of 130 nm (hereinafter referred to as an L/S pattern).

The following evaluation was performed, and the results are shown in Table 16. (LER)

As for L/S patterns (1:1) of 130 nm, 3σ was measured, which is a measure of indicating LER. Herein, 3σ is 3 times value (3σ) of a standard deviation (σ) calculated from the results which are obtained by measuring the widths of a sampled resist pattern in 32 points using the length-measuring SEM (manufactured by Hitachi Ltd., trade name: "S-9220"). The lower 3σ means that a resist pattern with the smaller roughness and even width is obtained.

TABLE 16

|  | LER (3σ) (nm) |
|---|---|
| Example 28 | 4.8 |
| Comparative example 11 | 9.3 |

When the results of Examples 22 to 27 were compared with those of Comparative example 10, it was found that the resist compositions in Examples 22 to 27 were excellent in exposure margin because they had a structural unit of the present invention.

Also, when the results of Example 28 were compared with those of Comparative example 11, it was found that the resist composition in Example 28 was very excellent in LER.

Synthesis Example 27

In 200 mL of tetrahydrofuran, 21.0 g of (4-oxo-2-adamantyloxy)methyl methacrylate (corresponding to the compound 5 in Synthesis example 5), 13.6 g of γ-butyrolactone methacrylate (GBLMA), and 9.5 g of 3-hydroxy-1-adamantyl methacrylate were dissolved, and then 1.64 g of azobisisobutylonitrile was added. After refluxing for 12 hours, the reaction solution was added dropwise to 1 L of n-heptane. The precipitated resin was separated by filtration and dried under reduced pressure, and then a white powder resin was obtained. This resin is referred to as the resin 22 and represented by the structural formula described below. The weight average molecular weight (Mw) and the degree of dispersion (Mw/Mn) of the resin 22 were 10,200 and 1.72, respectively. Also, the carbon 13 nuclear magnetic resonance spectra (¹³C-NMR) were measured, and the results showed that the composition ratio of the structural units represented by the structural formula described below was m:n:l=0.4:0.4:0.2 (mol %).

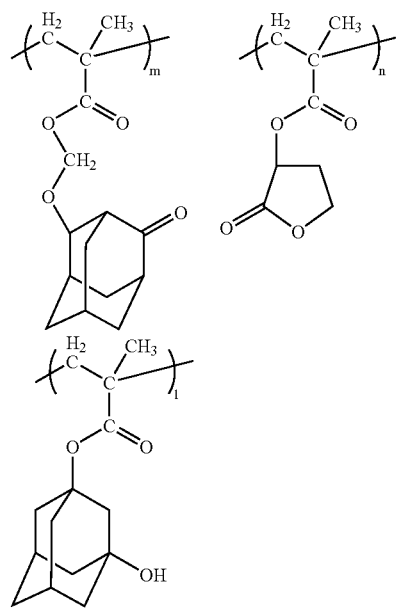

Synthesis Example 28

In 200 mL of tetrahydrofuran, 15.7 g of (4-oxo-2-adamantyloxy)methyl methacrylate (corresponding to the compound 5 in Synthesis example 5), 17.0 g of γ-butyrolactone methacrylate (GBLMA), and 9.5 g of 3-hydroxy-1-adamantyl methacrylate were dissolved, and then 1.64 g of azobisisobutylonitrile was added. After refluxing for 12 hours, the reaction solution was added dropwise to 1 L of n-heptane. The precipitated resin was separated by filtration and dried under reduced pressure, and then a white powder resin was obtained. This resin is referred to as the resin 23 and represented by the structural formula described above. The weight average molecular weight (Mw) and the degree of dispersion (Mw/Mn) of the resin 23 were 9,800 and 1.60, respectively. Also, the carbon 13 nuclear magnetic resonance spectra (¹³C-NMR) were measured, and the results showed that the composition ratio of the structural units represented by the structural formula described above was m:n:l=0.3:0.5:0.2 (mol %).

Example 29

The positive photoresist composition, which has the following composition, was prepared.

| (A) Resin: resin 22 | 100 parts by mass |
|---|---|
| (B) Acid generator: TPS-PFBS | 3.0 parts by mass |
| (D) Nitrogen-containing organic compound: triethanolamine | 0.35 parts by mass |
| Organic solvent: PGMEA:EL = 6:4 | 750 parts by mass |

Subsequently, an organic anti-reflective film material (trade name "ARC-29", manufactured by Brewer Science Ltd.) was coated on top of an 8-inch diameter silicon wafer and baked at 205° C. for 60 seconds, thereby forming an anti-reflective film with a film thickness of 38 nm as a substrate.

On the substrate, the aforementioned positive photoresist composition was uniformly coated by using a spinner and then dried by prebaking at 95° C. for 90 seconds, thereby forming a resist layer with a film thickness of 225 nm. Subsequently, the resist layer was selectively exposed by using the ArF exposure apparatus (wavelength: 193 nm) NSR-S302 (manufactured by Nikon Corporation, NA (numerical aperture)=0.60, ⅔ annular) through a binary mask.

Then, the exposed photoresist was subjected to a PEB treatment at 105° C. for 90 seconds followed by puddle development for 30 seconds at 23° C. in a 2.38% by mass aqueous solution of tetramethylammonium hydroxide, rinsed with pure water for 30 seconds, and then dried by shaking so as to form a resist pattern of line and space (1:1) of 140 nm. In this time, the sensitivity was 23 mJ/cm$^2$, and the exposure margin was 15.4%.

When Example 29 was compared with Comparative example 10, it was found that the resist composition in Example 29 was excellent in exposure margin.

INDUSTRIAL APPLICABILITY

As described above, a polymer compound of the present invention is useful for formation of a fine pattern excellent in rectangularity, specifically a fine pattern for exposure of a KrF, ArF, or F$_2$ laser.

The invention claimed is:
1. A polymer compound comprising:
an alkali soluble group (i), wherein
at least one hydrogen atom of the alkali soluble group (i) is substituted by an acid dissociable, dissolution inhibiting group (ii) represented by a general formula (1):

(1)

(wherein R$_1$ represents a cycloaliphatic group which contains at least one hydrophilic group and no more than 20 carbon atoms and may contain an oxygen atom, a nitrogen atom, a sulfur atom, or a halogen atom, and n represents 0 or an integer of 1 to 5), wherein the cycloaliphatic group contains an adamantane backbone, and wherein
the polymer compound exhibits changed alkali solubility under the action of an acid.

2. A polymer compound according to claim 1, wherein the alkali soluble group (i) is at least one selected from the group consisting of an alcoholic hydroxyl group, a phenolic hydroxyl group, and a carboxyl group.

3. A polymer compound according to claim 2, wherein a carbon atom adjacent to the carbon atom bonded to the alcoholic hydroxyl group is bonded to at least one fluorine atom.

4. A polymer compound according to claim 1, wherein the hydrophilic group is at least one selected from the group consisting of a carbonyl group, an ester group, an alcoholic hydroxyl group, ether, an imino group, and an amino group.

5. A compound represented by a general formula (3):

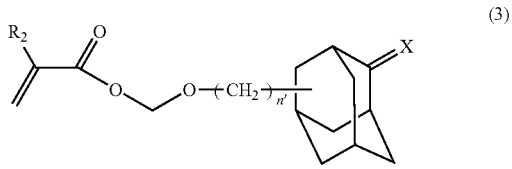

(3)

(wherein R$_2$ represents a hydrogen atom, a fluorine atom, a lower alkyl group containing 1 to 20 carbon atoms, or a fluorinated lower alkyl group containing 1 to 20 carbon atoms, X represents two hydrogen atoms or an oxygen atom, and n' represents 0 or 1).

6. A polymer compound comprising a structural unit (a1) derived from the compound according to claim 5.

7. A polymer compound according to claim 6, further comprising a structural unit (a3) derived from (meth)acrylate containing a lactone-containing monocyclic or polycyclic group.

8. A polymer compound according to claim 7, wherein the structural unit (a3) comprises at least two mutually different structural units derived from (meth)acrylate containing a lactone-containing monocyclic or polycyclic group.

9. A polymer compound according to claim 7, further comprising a structural unit (a4) derived from (meth)acrylate containing a polar group-containing polycyclic group.

10. A polymer compound comprising a structural unit (1) derived from a compound represented by a general formula (2):

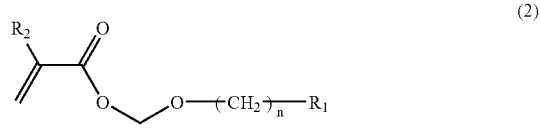

(2)

(wherein R$_1$ represents a cycloaliphatic group which contains no more than 20 carbon atoms and may contain an oxygen atom, a nitrogen atom, a sulfur atom, or a halogen atom; n represents 0 or an integer of 1 to 5; and R$_2$ represents a hydrogen atom, a fluorine atom, a lower alkyl group containing 1 to 20 carbon atoms, or a fluorinated lower alkyl group containing 1 to 20 carbon atoms), and a structural unit (a6) represented by a general formula (4):

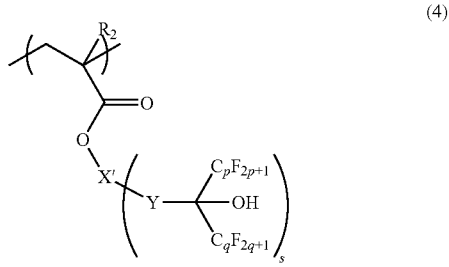

(4)

(wherein R$_2$ represents a hydrogen atom, a fluorine atom, a lower alkyl group containing 1 to 20 carbon atoms, or a fluorinated lower alkyl group containing 1 to 20 carbon atoms, X' represents a divalent or trivalent cyclic group, Y represents an alkylene or alkyleneoxy group containing 1 to 6 carbon atoms which is divalent, p and q independently represent an integer of 1 to 5, and s represents an integer of 1 or 2).

11. A polymer compound comprising a structural unit (a1) derived from the compound represented by a general formula (2):

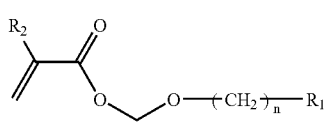

(2)

(wherein $R_1$ represents a cycloaliphatic group which contains no more than 20 carbon atoms and may contain an oxygen atom, a nitrogen atom, a sulfur atom, or a halogen atom; n represents 0 or an integer of 1 to 5; and $R_2$ represents a hydrogen atom, a fluorine atom, a lower alkyl group containing 1 to 20 carbon atoms, or a fluorinated lower alkyl group containing 1 to 20 carbon atoms), and a structural unit (a3) derived from (meth)acrylate containing a lactone-containing monocyclic or polycyclic group, wherein the structural unit (a3) comprises (meth)acrylate containing a lactone-containing monocyclic group and (meth)acrylate containing a lactone-containing polycyclic group represented by a following structural formula (47).

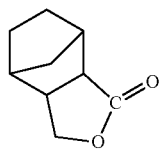

(47)

12. A photoresist composition comprising:
a base material resin component (A) which exhibits changed alkali solubility under the action of an acid; and an acid generator component (B) which generates the acid on exposure to radiation, wherein the base material resin component (A) is a polymer compound comprising:

a structural unit (a1) derived from the compound represented by a general formula (2):

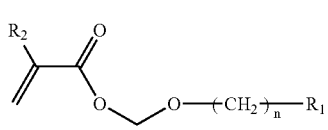

(2)

(wherein $R_1$ represents a cycloaliphatic group which contains no more than 20 carbon atoms and may contain an oxygen atom, a nitrogen atom, a sulfur atom, or a halogen atom; n represents 0 or an integer of 1 to 5; and $R_2$ represents a hydrogen atom, a fluorine atom, a lower alkyl group containing 1 to 20 carbon atoms, or a fluorinated lower alkyl group containing 1 to 20 carbon atoms), and a structural unit (a3) derived from (meth)acrylate containing a lactone-containing monocyclic or polycyclic group, wherein the structural unit (a3) comprises (meth)acrylate containing a lactone-containing monocyclic group and (meth)acrylate containing a lactone-containing polycyclic group represented by a following structural formula (47).

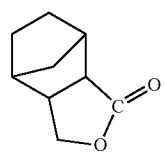

(47)

13. A resist pattern formation method comprising:
forming a photoresist film on a substrate using the photoresist composition according to claim 12;
exposing the photoresist film; and developing the exposed photoresist film to form a resist pattern.

* * * * *